United States Patent
Shi

(10) Patent No.: US 11,013,753 B2
(45) Date of Patent: May 25, 2021

(54) TLX AND MIR-219 AS POTENTIAL THERAPEUTIC TARGETS FOR NEURODEVELOPMENTAL DISORDERS

(71) Applicant: CITY OF HOPE, Duarte, CA (US)

(72) Inventor: Yanhong Shi, Arcadia, CA (US)

(73) Assignee: CITY OF HOPE, Duarte, CA (US)

( * ) Notice: Subject to any disclaimer, the term of this patent is extended or adjusted under 35 U.S.C. 154(b) by 195 days.

(21) Appl. No.: 16/083,849

(22) PCT Filed: Mar. 10, 2017

(86) PCT No.: PCT/US2017/021962
§ 371 (c)(1),
(2) Date: Sep. 10, 2018

(87) PCT Pub. No.: WO2017/156491
PCT Pub. Date: Sep. 14, 2017

(65) Prior Publication Data
US 2019/0060349 A1 Feb. 28, 2019

Related U.S. Application Data

(60) Provisional application No. 62/307,367, filed on Mar. 11, 2016, provisional application No. 62/306,631, filed on Mar. 10, 2016.

(51) Int. Cl.
| | |
|---|---|
| *C07H 21/04* | (2006.01) |
| *A61K 31/7105* | (2006.01) |
| *C07K 14/705* | (2006.01) |
| *C12N 15/85* | (2006.01) |
| *C12N 15/113* | (2010.01) |
| *A61P 25/18* | (2006.01) |
| *C12N 15/115* | (2010.01) |
| *A61P 25/24* | (2006.01) |
| *C12N 5/07* | (2010.01) |

(52) U.S. Cl.
CPC .......... *A61K 31/7105* (2013.01); *A61P 25/18* (2018.01); *A61P 25/24* (2018.01); *C07K 14/70567* (2013.01); *C12N 5/06* (2013.01); *C12N 15/113* (2013.01); *C12N 15/115* (2013.01); *C12N 15/85* (2013.01); *C12N 2310/113* (2013.01); *C12N 2310/13* (2013.01); *C12N 2310/14* (2013.01)

(58) Field of Classification Search
None
See application file for complete search history.

(56) References Cited

U.S. PATENT DOCUMENTS

2006/0040321 A1 2/2006 Shi et al.
2010/0227908 A1 9/2010 Cairns

OTHER PUBLICATIONS

Abmayr, S. M., et al., "Preparation of nuclear and cytoplasmic extracts from mammalian cells," Curr. Protoc. Pharmacol. 12.3.1-12.3.13 (2001).
Bartel, D. P., "MicroRNAS: Genomics, biogenesis, mechanism, and function," Cell 116:281-297 (2004).
Berezikov, E., et al., "Mammalian mirtron genes," Mol. Cell. 28(2):328-336 (2007).
Beveridge, N. J., et al., "Dysregulation of miRNA 181b in the temporal cortex in schizophrenia," Hum. Mol. Genet. 17(8):1156-1168 (2008).
Beveridge, N. J., et al., "Schizophrenia is associated with an increase in cortical microRNA biogenesis," Mol. Psych. 15:1176-1189 (2010).
Brennand, K. et al., "Phenotypic differences in hiPSC NPCs derived from patients with schizophrenia," Mol. Psych. 20:361-368 (2015).
Cheng, H.Y. M., et al., "microRNA modulation of circadian clock period and entrainment," Neuron 54(5):813-829 (2007).
Chiang, C-H., et al., "Integration-free induced pluripotent stem cells derived from schizophrenia patients with a DISC1 mutation," Mol. Psych. 16(4):358-360 (2011).
Clapcote, S. J. et al., "Behavioral phenotypes of Disc1 missense mutations in mice," Neuron 54:387-402 (2007).
Davis, B. N., et al., "SMAD proteins control DROSHA-mediated microRNA maturation," Nature 454(7200):56-61 (2008).
Dugas, J. C., et al., "Dicer1 and miR-219 are required for normal oligodendrocyte differentiation and myelination," Neuron 65(5):597-611 (2010).
Ellison-Wright, I., et al., "The anatomy of first-episode and chronic schizophrenia: An anatomical likelihood estimation meta-analysis," Am. J. Psych. 165(8):1015-1023 (2008).
Elmi, M., et al., "TLX activates MASH1 for induction of neuronal lineage commitment of adult hippocampal neuroprogenitors," Mol. Cell. Neurosci. 45:121-131 (2010).
Flagstad, P., et al., "Disruption of neurogenesis on gestational day 17 in the rat causes behavioral changes relevant to positive and negative schizophrenia symptoms and alters amphetamine-induced dopamine release in nucleus accumbens," Neuropsychopharmacology 29:2052-2064 (2004).
Fukuda, T., et al., "DEAD-box RNA helicase subunits of the Drosha complex are required for processing of rRNA and a subset of microRNAs," Nat. Cell Biol. 9:604-611 (2007) and retracted online Oct. 31, 2014.
Fuller-Pace, F. V., et al., "The DEAD box RNA helicases p68 (Ddx5) and p72 (Ddx17):novel transcriptional co-regulators," Biochem. Soc. Trans. 36:609-612 (2008).
Goldberg, J.F., et al., "Identifying and treating cognitive impairment in bipolar disorder," Bipolar Disorders 11(Suppl. 2):123-137 (2009).
Gregory, R. I., et al., "The microprocessor complex mediates the genesis of microRNAs," Nature 432:235-240 (2004).

(Continued)

Primary Examiner — Kimberly Chong
(74) Attorney, Agent, or Firm — Perkins Coie LLP; Lara Dueppen; Yang Tang

(57) ABSTRACT

Disclosed herein are methods of treating neurodevelopmental disorders such as schizophrenia (SCZ), bipolar disorder or depression. The methods entail inhibiting expression of miR-219 or overexpressing TLX thereby promoting proliferation of neural stem cells (NSCs) in the subjects.

11 Claims, 17 Drawing Sheets

Specification includes a Sequence Listing.

(56) References Cited

OTHER PUBLICATIONS

Haraguchi, T., et al., "Vectors expressing efficient RNA decoys achieve the long-term suppression of specific microRNA activity in mammalian cells," Nucleic Acids Res. 37(6):e43 (2009).
Hikida, T., et al., "Dominant-negative DISC1 transgenic mice display schizophrenia-associated phenotypes detected by measures translatable to humans," PNAS 104(36):14501-14506 (2007).
Hudish, L. I., et al., "miR-219 regulates neural precursor differentiation by direct inhibition of apical par polarity proteins," Dev. Cell 27:387-398 (2013).
Ishizuka, K., et al., "DISC1-dependent switch from progenitor proliferation to migration in the developing cortex," Nature 473(7345):92-96 (2011).
Iwahara, N., et al., "Transcriptional activation of NAD+-dependent protein deacetylase SIRT1 by nuclear receptor TLX," Biochem. Biophys. Res. Commun. 386:671-675 (2009).
Jackson, E. L., et al., "PDGFRalpha-positive B cells are neural stem cells in the adult SVZ that form glioma-like growths in response to increased PDGF signaling," Neuron 51:187-199 (2006).
Kawai, S., et al., "BRCA1 regulates microRNA biogenesis via the DROSHA microprocessor complex," J. Cell Biol. 197(2):201-208 (2012).
Keene, J. D., et al., "RIP-Chip: the isolation and identification of mRNAs, microRNAs and protein components of ribonucleoprotein complexes from cell extracts," Nat. Protoc. 1(1):302-307 (2006).
Kim, J. Y., et al., "DISC1 regulates new neuron development in the adult brain via modulation of AKT-mTOR signaling through KIAA1212," Neuron 63(6):761-773 (2009).
Kocerha, J., et al., "MicroRNA-219 modulates NMDA receptor-mediated neurobehavioral dysfunction," PNAS 106(9):3507-3512 (2009).
Koike, H., et al., "Disc1 is mutated in the 129S6/SvEv strain and modulates working memory in mice," PNAS 103(10):3693-3697 (2006).
Kvajo, M., et al., "A mutation in mouse Disc1 that models a schizophrenia risk allele leads to specific alterations in neuronal architecture and cognition," PNAS 105(19):7076-7081 (2008).
Lee, Y., et al., "The nuclear RNase III Drosha initiates microRNA processing," Nature 425:415-419 (2003).
Li, W., et al., "Specific developmental disruption of disrupted-in-schizophrenia-1 function results in schizophrenia-related phenotypes in mice," PNAS 104(46):18280-18285 (2007).
Li, W., et al., "Nuclear receptor TLX regulates cell cycle progression in neural stem cells of the developing brain," Mol. Endocrinol. 22(1):56-64 (2008).
Lukiw, W. J., "Micro-RNA speciation in fetal, adult and Alzheimer's disease hippocampus," NeuroReport 18:297-300 (2007).
Mao, Y., et al., "DISC1 regulates neural progenitor proliferation via modulation of GSK3beta/beta-catenin signaling," Cell 136(6):1017-1031 (2009).
Monaghan, A. P., et al., "Defective limbic system in mice lacking the tailless gene," Nature 390:515-517 (1997).
Murai, K., et al., "Nuclear receptor TLX stimulates hippocampal neurogenesis and enhances learning and memory in a transgenic mouse model," PNAS 111(25):9115-9120 (2014).
Murai, K., et al., "The TLX-miR-219 cascade regulates neural stem cell proliferation in neurodevelopment and schizophrenia iPSC model," Nat. Commun. 7:10965 (2016).
Newton, S. S., et al., "Neurogenic actions of atypical antipsychotic drugs and therapeutic implications," CNS Drugs 21(9):715-725 (2007).
Niwa, M., et al., "Knockdown of DISC1 by in utero gene transfer disturbs postnatal dopaminergic maturation in the frontal cortex and leads to adult behavioral deficits," Neuron 65(4):480-489 (2010).
Olde Loohuis, N. F. M., et al., "MicroRNA networks direct neuronal development and plasticity," Cell. Mol. Life Sci. 69:89-102 (2012).
Pletnikov, M.V., et al., "Enlargement of the lateral ventricles in mutant DISC1 transgenic mice," Mol. Psych. 13:115 (2008).

Qu, Q., et al., "Orphan nuclear receptor TLX activates Wnt/beta-catenin signalling tostimulate neural stem cell proliferation and self-renewal," Nat. Cell Biol. 12(1):31-39 (2010).
Reif, A., et al., "Neural stem cell proliferation is decreased in schizophrenia, but not in depression," Mol. Psych. 11:514-522 (2006).
Rivers, L. E., et al., "PDGFRA/NG2 glia generate myelinating oligodendrocytes and piriform projection neurons in adult mice," Nat. Neurosci. 11(12):1392-1401 (2008).
Roy, K., et al., "The Tlx gene regulates the timing of neurogenesis in the cortex," J. Neurosci. 24(38):8333-8345 (2004).
Sachs, N.A., et al., "A frameshift mutation in Disrupted in Schizophrenia 1 in an American family with schizophrenia and schizoaffective disorder," Mol. Psych. 10:758-764 (2005).
Santarelli, D. M., et al., "Upregulation of dicer and microRNA expression in the Dorsolateral Prefrontal Cortex Brodmann Area 46 in schizophrenia," Biol. Psych. 69:180-187 (2011).
Sarachana, T., et al., "Investigation of post-transcriptional gene regulatory networks associated with autism spectrum disorders by microRNA expression profiling of lymphoblastoid cell lines," Genome Med. 2:23 (2010).
Saus, E., et al., "Genetic variants and abnormal processing of pre-miR-182, a circadian clock modulator, in major depression patients with late insomnia," Hum. Mol. Genet. 19(20):4017-4025 (2010).
Shen, S., et al., "Schizophrenia-related neural and behavioral phenotypes in transgeneic mice expressing truncated Disc1," J. Neurosci. 28(43):10893-10904 (2008).
Shi, Y., et al., "Expression and function of orphan nuclear receptor TLX in adult neural stem cells," Nature 427:78-83 (2003).
Smalheiser, N. R., et al., "Expression of microRNAs and other small RNAs in prefrontal cortex in schizophrenia, bipolar disorder and depressed subjects," PLoS One 9(1):e86469 (2014).
Stenman, J. M., et al., " Tlx controls proliferation and patterning of lateral telencephalic progenitor domains," J. Neurosci. 23(33):10568-10576 (2003).
Sun, G., et al., "Molecular properties, functional mechanisms, and applications of sliced siRNA," Mol. Ther. Nucl. Acids 4:e221 (2015).
Sun, G.Q., et al., "Orphan nuclear receptor TLX recruits histone deacetylases to repress transcription and regulate neural stem cell proliferation," PNAS 104(39):15282-15287 (2007).
Sun, G.Q., et al., "Histone demethylase LSD1 regulates neural stem cell proliferation," Mol. Cell. Biol. 30(8):1997-2005 (2010).
Sun, G.Q., et al., "miR-137 forms a regulatory loop with nuclear receptor TLX and LSD1 in neural stem cells," Nat. Commun. 2:529 (2011).
Suzuki, H. I., et al., "Modulation of microRNA processing by p53," Nature 460:529-534 (2009).
Swayze, V. W., et al., "Structural brain abnormalities in bipolar affective disorder," Arch. Gen. Psych. 47:1054-1059 (1990).
Thomas, M., et al., "PEI-complexed LNA antiseeds as miRNA inhibitors," RNA Biol. 9(8):1088-1098 (2012).
United States Patent and Trademark Office, International Search Report and Written Opinion dated Jun. 16, 2017 for PCT/US17/21962.
Wen, Z., et al., "Synaptic dysregulation in a human iPS cell model of mental disorders," Nature 515(7527):414-418 (2014).
Yokoyama, A., et al., "Transrepressive function of TLX requires the histone demethylase LSD1," Mol. Cell. Biol. 28(12):3995-4003 (2008).
Yoon, K.J., et al., "Modeling a genetic risk for schizophrenia in iPSCs and mice reveals neural stem cell deficits associated with adherens junctions and polarity," Cell Stem Cell 15(1):79-91 (2014).
Young, K. A., et al., "Fierce: a new mouse deletion of Nr2e1; violent behavior and ocular abnormalities are background-dependent," Behav. Brain Res. 132(2):145-158 (2002).
Yu, R. T., et al., "Relationship between *Drosophila* gap gene tailless and a vertebrate nuclear receptor Tlx," Nature 370:375-379 (1994).
Zhang, C.L., et al., "A role for adult TLX-positive neural stem cells in learning and behavior," Nature 451:1004-1009 (2008).
Zhao, C., et al., "A feedback regulatory loop involving microRNA-9 and nuclear receptor TLX in neural stem cell fate determination," Nat. Struct. Mol. Biol. 16(4):365-371 (2009).

(56) References Cited

OTHER PUBLICATIONS

Zhao, C., et al., "MicroRNA let-7b regulates neural stem cell proliferation and differentiation by targeting nuclear receptor TLX signaling," PNAS 107(5):1876-1881 (2010).

Zhao, X., et al., "MicroRNA-mediated control of oligodendrocyte differentiation," Neuron 65(5):612-626 (2010).

Figure 16

| Gene | Strand | Sequence | Assay | SEQ ID NO: |
|---|---|---|---|---|
| miR-219 | Antisense | 5'-AGAATTGCGTTTGGACAATCA-3' | Northern blot | 1 |
| U6 | Antisense | 5'-TATGGAACGCTTCTCGAATT-3' | Northern blot | 2 |
| mTLX | Forward | 5'-GTCTTTACAAGATCAGCTGATG-3' | RT-PCR | 3 |
| | Reverse | 5'-ATGTCACTGGATTTGTACATATC-3' | RT-PCR | 4 |
| pri-miR-219-1 | Forward | 5'-TTTCCCACGCCAGACATTCAC-3' | RT-PCR | 5 |
| | Reverse | 5'-GATCCCCAACTTCTCTCAAGC-3' | RT-PCR | 6 |
| pri-miR-219-2 | Forward | 5'-TTGCCGAGCTTCTGCGAGGTA-3' | RT-PCR | 7 |
| | Reverse | 5'-TGTCCCCTCTTTGCATGCCAG-3' | RT-PCR | 8 |
| PDGFRα | Forward | 5'-CAAACCTGACCATGCCACCAG-3' | RT-PCR | 9 |
| | Reverse | 5'-TCTCGATGGCACTCTCTTCCG-3' | RT-PCR | 10 |
| RORβ | Forward | 5'-TACGTGGTGGAGTTCGCCAAG-3' | RT-PCR | 11 |
| | Reverse | 5'-CCCATGCAAGTTGCAGACTGC-3' | RT-PCR | 12 |
| LMO3 | Forward | 5'-GTTTGGTGTAACGGGAAACTGCG-3' | RT-PCR | 13 |
| | Reverse | 5'-TCCTCGTAGTCTGTCTGGCAAAG-3' | RT-PCR | 14 |
| HMGA2 | Forward | 5'-ACATCAGCCCAGGGACAACCT-3' | RT-PCR | 15 |
| | Reverse | 5'-CAAGAGTCCGCAGAGGAGGAT-3' | RT-PCR | 16 |
| EphrinB2 | Forward | 5'-TTCAGCCCTAACCTCTGGGGT-3' | RT-PCR | 17 |
| | Reverse | 5'-AACCCAGGAGATTGTTCCCGG-3' | RT-PCR | 18 |
| mGAPDH | Forward | 5'-CATCACCATCTTCCAGGAGC-3' | RT-PCR | 19 |
| | Reverse | 5'-GCTGTAGCCGTATTCATTGTC-3' | RT-PCR | 20 |
| pri-miR-219-2 | Forward | 5'-TACGCAGCTCCCGAGATCTGGTG-3' | RT-PCR | 21 |
| | Reverse | 5'-CAGCGTGGACCTCGTCTCTGTAG-3' | RT-PCR | 22 |
| pre-miR-219-2 | Forward | 5'-CTGATTGTCCAAACGCAATTCTTG-3' | RT-PCR | 23 |
| | Reverse | 5'-CAGATGTCCAGCCACAATTCTC-3' | RT-PCR | 24 |
| PDGFRα | Forward | 5'-GTGGCCTGGACGAACAGAGACT-3' | RT-PCR | 25 |
| | Reverse | 5'-GGAACCTGTCTCGATGGCACTC-3' | RT-PCR | 26 |
| m TLX | Forward | 5'-GGTTCAGACAGCTCCGATTAGAC-3' | RT-PCR | 27 |
| | Reverse | 5'-TGGAGAGCGGCAATGGCGGCAGC-3' | RT-PCR | 28 |
| β-Actin | Forward | 5'-CCGAGCGTGGCTACAGCTTC-3' | RT-PCR | 29 |
| | Reverse | 5'-ACCTGGCCGTCAGGCAGCTC-3' | RT-PCR | 30 |
| hTLX | Forward | 5'-CTAAGAGTGTGCCAGCCTTC-3' | RT-PCR | 31 |
| | Reverse | 5'-TGTTAGCATCAACCGGAATGG-3' | RT-PCR | 32 |
| hGAPDH | Forward | 5'-CCTGTTCGACAGTCAGCCG-3' | RT-PCR | 33 |
| | Reverse | 5'-CGACCAAATCCGTTGACTC-3' | RT-PCR | 34 |

TLX AND MIR-219 AS POTENTIAL THERAPEUTIC TARGETS FOR NEURODEVELOPMENTAL DISORDERS

PRIORITY CLAIM

This application claims priority to U.S. Provisional Application No. 62/306,631, filed Mar. 10, 2016, and U.S. Provisional Application No. 62/307,367, filed Mar. 11, 2016, both of which are incorporated by reference herein, including drawings.

STATEMENT OF GOVERNMENT FUNDING

This work was supported by Sidell Kagan Foundation and California Institute for Regenerative Medicine TR2-01832 and RB4-06277. Research included work performed in Integrative Genomics and Drug Discovery & Structural Biology Cores supported by the National Cancer Institute of the National Institutes of Health under award number P30CA33572.

BACKGROUND

TLX is a nuclear receptor that plays a critical role in vertebrate brain function [1-3]. It is an essential regulator of adult neural stem cell (NSC) self-renewal [3-5] and plays an important role in enhancing learning and memory by regulating adult hippocampal neurogenesis [6,7]. It also plays a role in neurodevelopment through regulation of cell cycle progression in embryonic NSCs [4,8-10]. TLX is a well-characterized transcriptional regulator. It controls target gene expression partly by recruiting transcriptional corepressors, such as HDACs and LSD1 [11-13]. TLX represses the transcription of GFAP, p21, pten, and microRNAs miR-9 and miR-137, but activates Wnt signaling, SIRT1 and MASH1 in NSCs [3,5,11,12,14-16]. However, the function of TLX in regulating gene expression beyond transcriptional regulation has not been reported.

microRNAs (miRNAs) are small non-coding RNAs that regulate gene expression through translational inhibition or RNA degradation [17]. The biogenesis of miRNAs starts from primary transcripts (pri-miRNAs), which are processed by the nuclear RNaseIII Drosha into precursor miRNAs (pre-miRNAs) that contain hairpin loop structures. The pre-miRNAs are exported to the cytoplasm and further processed into mature miRNAs by the cytoplasmic RNaseIII Dicer. Mature miRNAs are incorporated into an RNA-induced silencing complex (RISC) to repress target mRNAs. The Drosha complex consists of Drosha, DiGeorge syndrome critical gene 8 (DGCR8), RNA helicase p68 (DDX5) and p72 (DDX17) [18-20]. Recent studies reported that SMAD, p53, and BRCA1 bind to Drosha and promote the processing activity of Drosha [21-23]. However, little is known about the physiological effect of miRNA processing.

miR-219 is an miRNA that is specifically expressed in the brain [24,25]. It promotes oligodendrocyte differentiation by repressing negative regulators of oligodendrocyte differentiation [26,27]. In a recent study, miR-219 was shown to promote neural precursor cell differentiation in zebrafish by inhibiting apical polarity proteins, par-3 family cell polarity regulator (PARD) and protein kinase C iota (PRKCI) [28]. However, whether miR-219 regulates the phenotypes of neural stem/progenitor cells (collectively referred to as NSCs) in mammalian brains remains unknown.

Several studies analyzing miRNA levels in postmortem brains from schizophrenia (SCZ) patients reported an increase in the expression of a set of miRNAs in SCZ patients [29-31]. miR-219 is among the most highly up-regulated miRNAs in brain regions of SCZ patients [29,30,32]. However, the functional relevance of elevated miR-219 expression in SCZ brain cells remains unknown.

SUMMARY

In one aspect, this disclosure relates to a method for treating a neurodevelopmental disorder in a subject. The method entails inhibiting, repressing, or down-regulating expression of miR-219, overexpressing or up-regulating the expression of TLX, or a combination thereof. In some embodiments, the expression of miR-219 is inhibited, repressed or down-regulated by administering to the subject a therapeutically effective amount of one or more antagonists of miR-219. In some embodiments, expression of TLX is up-regulated by administering to the subject a therapeutically effective amount of one or more TLX agonists or a vector expressing a gene encoding TLX.

BRIEF DESCRIPTION OF THE DRAWINGS

FIG. 1a shows elevated expression of mature miR-219 in TLX KO mouse brains, compared to WT mouse brains, revealed by Northern blot analysis. U6 is included as a loading control. FIG. 1b shows the levels of the two primary forms of miR-219, pri-miR-219-1 and pri-miR-219-2, exhibited minimal change in WT and TLX KO mouse brains, as analyzed by RT-PCR. FIG. 1c shows the levels of pre-miR-219 and mature miR-219, but not pri-miR-219, increased significantly in TLX KO mouse brains. n=3. FIG. 1d shows the levels of pre-miR-219 and mature miR-219, but not pri-miR-219, increased significantly in TLX knockdown NSCs independent of actinomycin D treatment. siC: control RNA; siTLX: TLX siRNA. n=6. FIG. 1e shows a scheme for monitoring miRNA processing using a luciferase reporter. The miRNA processing activity is inversely correlated with the luciferase activity. FIG. 1f shows overexpression of TLX inhibits miR-219 processing from pri-miR-219 to pre-miR-219. miR-1224-Glo was included as a negative control. The firefly luciferase activity was normalized with the Renilla luciferase internal control. The relative luciferase activity is shown. C: control vector. n=4. FIG. 1g shows knockdown of TLX promotes miR-219 processing from pri-miR-219 to pre-miR-219. The relative luciferase activity in NSCs transfected with a vector expressing siC or siTLX, together with the control-Glo, miR-219-Glo reporter, or miR-1224 Glo reporter control. n=4. *p<0.05, p<0.01, *p<0.001 by student's t-test, and n represents experimental repeats in panels c, d, f & g. Error bars are sd of the mean for all the quantification in this study. For each representative image, the experiments were repeated three times or more.

FIG. 2a shows a scheme for identifying TLX-interacting proteins using mass spectrometry (MS) analysis. FIG. 2b shows differentially represented proteins in the HA immunoprecipitates of control HA or HA-TLX-expressing HeLa cells. Arrow indicates a protein band of 68 kD that is specifically detected in the HA immunoprecipitates of HA-TLX-expressing HeLa cells. FIG. 2c shows interaction of TLX with p68, Drosha and DGCR8. Lysates of HA-TLX transfected HEK293T cells were treated with or without DNase and RNase, then immunoprecipitated with HA antibody or IgG control. The immunoprecipitates were blotted with p68 antibody. In parallel, lysates of Flag-Drosha and HA-TLX or Flag-DGCR8 and HA-TLX co-transfected HEK293T cells were treated with or without DNase and RNase. Cell lysates were immunoprecipitated with anti-Flag antibody, then blotted with anti-HA antibody. FIG. 2d shows interaction of TLX with Drosha and DGCR8 in mouse brains. Lysates of embryonic mouse brains were immunoprecipitated with TLX antibody, then blotted with anti-Drosha, anti-DGCR8 or anti-TLX antibody. FIG. 2e shows a scheme for RNA immunoprecipitation. Lysates of NSCs transduced with TLX siRNA were immunoprecipitated with anti-Drosha, anti-DGCR8, or anti-TLX antibody. RNAs were extracted from the immunoprecipitates, and subjected to RT-PCR for pri-miR-219. FIG. 2f shows TLX knockdown promoted the binding of Drosha and DGCR8 to pri-miR-219. Lysates of NSCs transduced with siC or siTLX were immunoprecipitated with IgG control or indicated antibodies. pri-miR-219 RNA associated with Drosha (indicated by solid arrows) or DGCR8 (indicated by open arrows) was determined by RT-PCR.

FIGS. 3a and 3b show overexpressing miR-219 in NSCs inhibited cell proliferation (FIG. 3a) and promoted neuronal differentiation (FIG. 3b). BrdU or Tuj1 staining is shown in red and Dapi counterstaining is shown in blue. FIGS. 3c and 3d show quantification of BrdU+cells (FIG. 3c) and Tuj1+ cells (FIG. 3d) in control RNA (C) and miR-219-treated NSCs. n=5, *p<0.001 by student's t-test for both panels. N represents experimental repeats. FIG. 3e. shows in utero electroporation of miR-219 decreased NSC proliferation in the VZ/SVZ of embryonic brains. Electroporated cells were labeled by RFP and proliferating cells were labeled by Ki67. FIG. 3f shows the percentage of RFP+Ki67+ cells out of total RFP+ cells in control RNA or miR-219-electroporated brains. n=3 mice per group. *p<0.01 by student's t-test. FIG. 3g shows electroporation of miR-219 induced precocious outward cell migration. The electroporated brains were stained for neuronal marker doublecortin (DCX). Transfected cells were labeled by RFP. FIG. 3h shows the percentage of electroporated cells (RFP+) that migrated to the CP. n=3 mice per group. *p<0.01 by student's t-test. FIG. 3i shows higher magnification images of RFP+DCX+ cells at the CP of brains electroporated with control RNA or miR-219. Scale bar: 50 μm for panels a, b, & e; 100 μm for panel g; 25 μm for panel i. FIG. 3j shows the percentage of Tbr1+RFP+ cells out of total RFP+ cells in control RNA or miR-219-electroporated brains. n=3 mice per group. *p<0.01 by student's t-test.

FIG. 4a shows co-electroporation of TLX siRNA with an miR-219 inhibitor rescued the decrease in NSC proliferation induced by TLX siRNA. E13.5 mouse brains were electroporated in utero with 1) a control RNA and the RFP reporter (siC-RFP), 2) TLX siRNA and the RFP reporter (siTLX-RFP), 3) an miR-219 inhibitor with siC-RFP, or 4) an miR-219 inhibitor with siTLX-RFP. The electroporated cells were labeled by RFP and proliferating cells were labeled by Ki67. FIG. 4b shows the percentage of RFP+Ki67+ cells out of total RFP+cells in electroporated brains described in panel e is shown. n=3 mice per group. *p<0.001 by student's t-test. FIG. 4c shows electroporation was performed as described in panel e and brain sections were stained for neuronal marker DCX. Migration of the electroporated cells was tracked by RFP fluorescence. FIG. 4d shows the percentage of electroporated cells (RFP+) that migrated to the CP in electroporated brains described in panel g is shown. n=3 mice per group. *p<0.05 and ** p<0.01 by student's t test. Scale bar: 50 μm for panel a; 200 μm for panel c.

FIG. 5a shows mapping p68 and Drosha-interacting domain in TLX. A schematic of TLX deletion mutants and the Drosha/p68 interacting domain (Dpi) is shown on the left. A summary of p68 and Drosha binding results is shown on the right. FIG. 5b shows deletion of TLX residues 340 to 359 reduced the interaction of TLX with p68 substantially. HEK293T cells were transfected with HA-tagged full length TLX (residues 1-385) or its deletion mutants (residues 1-306, 1-340, or 1-359). Lysates were immunoprecipitated (IP) with HA antibody (aHA), then probed with p68 antibody (ap68) in Western blot analysis (WB). FIG. 5c shows deletion of TLX residues 340 to 359 reduced TLX interaction with Drosha. HEK293T cells were transfected with Flag-tagged Drosha and HA-tagged full length or deletion mutants of TLX. Lysates were IP with Flag antibody (aFlag), then probed with HA antibody (aHA). A non-specific (ns) band in the Western blot was indicated. FIGS. 5d and 5e show expressing the Dpi peptide abolished the interaction of TLX with Drosha (FIG. 5d), but not the interaction of TLX with HDAC5 (FIG. 5e), as revealed by co-IP analysis. An empty vector (−) and a control peptide (C) were included as negative controls for the Dpi peptide. Cell lysates were IP with anti-Flag antibody, then blotted with anti-HA or anti-Flag antibody. The expression of individual proteins in the transfected cells was shown by immunoblotting as input. FIG. 5f shows expression of the Dpi peptide promotes miR-219 processing. miR-219 processing was monitored using the miR-219-Glo reporter. Expressing the Dpi peptide decreased miR-219-Glo activity compared to expressing the empty vector (−) or a control peptide (C). n=3. ***p<0.001 by student's t-test. FIGS. 5g-5i show the levels of pre-miR-219 (h) and mature miR-219 (FIG. 5i), but not pri-miR-219 (FIG. 5g), were increased by expressing the Dpi peptide, as revealed by RT-PCR. n=4 (g); n=4 (h); n=3 (i). *p<0.05, **p<0.01 by student's t-test in panels h & i. N represents experimental repeats in panels f-i.

FIGS. 6a-6c show expression of the Dpi peptide inhibits NSC proliferation and promotes neuronal differentiation, and this effect could be reversed by the miR-219 inhibitor, TuD-miR-219. Mouse embryonic NSCs were transduced with virus expressing the Dpi peptide or a control peptide (C), in the absence or presence of TuD-miR-219. The virus transduced cells were labeled by a GFP reporter. Cell proliferation was determined by the percentage of GFP+BrdU+ cells (BrdU+GFP+/GFP+) (FIG. 6b) and neuronal differentiation was determined by the percentage of GFP+Tuj1+ cells (Tuj1+GFP+/GFP+) (c). n=7 (b); n=5 (c). N represents experimental repeats. FIGS. 6d-6g show expression of Dpi inhibited NSC proliferation (FIGS. 6d and 6e), but promoted neuronal differentiation (FIGS. 6f and 6g) in mouse brains. E13.5 mouse brains were electroporated in utero with vectors expressing: 1) a control peptide and RFP reporter (C); 2) Dpi peptide and RFP reporter (Dpi); 3) TuD-miR-219 plus control peptide and RFP reporter (TuD-miR-219+C); or 4) TuD-miR-219 plus Dpi and RFP reporter (TuD-miR-219+Dpi). The electroporated cells were labeled by RFP, proliferating cells were labeled by Ki67 (FIG. 6e), and neuronal cells were labeled by DCX (FIG. 6f). The percentage of RFP+Ki67+ cells (FIG. 6e) or RFP+ cells that migrated to the CP (FIG. 6g) out of total RFP+ cells is shown. n=3 mice per group for panels e & g. *p<0.05, p<0.01, *p<0.001 by student's t-test for panels b, c, e & g. Scale bar: 100 µm for panel a; 50 µm for panel d; 200 µm for panel f.

FIGS. 7a-7f illustrate that the DISC1-mutant NSCs exhibit increased miR-219 expression and reduced proliferation. FIG. 7a shows a schematic diagram showing the pedigree for iPSC generation. iPSCs from a wild type (WT) individual outside of the pedigree (C1) were included as a control. The + and − signs represent the presence and absence of the 4 bp deletion in the DISC1 gene, respectively. The squares represent male, while the circles represent female. FIG. 7b shows NSCs derived from both WT (C1, C2, & C3) and DISC1-mutant iPSCs (D1, D2, C1M and C3M) expressed neural precursor markers SOX1 and NESTIN. Scale bar: 50 µm. FIGS. 7c and 7d show RT-PCR showing elevated expression of miR-219 (FIG. 7c) and reduced expression of TLX (FIG. 7d) in DISC-mutant NSCs (D1, D2, C1M and C3M), compared to that in WT NSCs (C1, C2, & C3). FIGS. 7e and 7f show the DISC1-mutant NSCs (D1, D2, C1M and C3M) exhibited reduced cell proliferation (FIG. 7e) and precocious neuronal differentiation (FIG. 7f). NSC proliferation rate was determined by the percentage of BrdU+SOX1+ cells. Neuronal differentiation rate was determined by the percentage of Tuj1+ cells. n=4 for panels c-f. N represents experimental repeats. ANOVA test result was shown below each graph.

Figure 8:
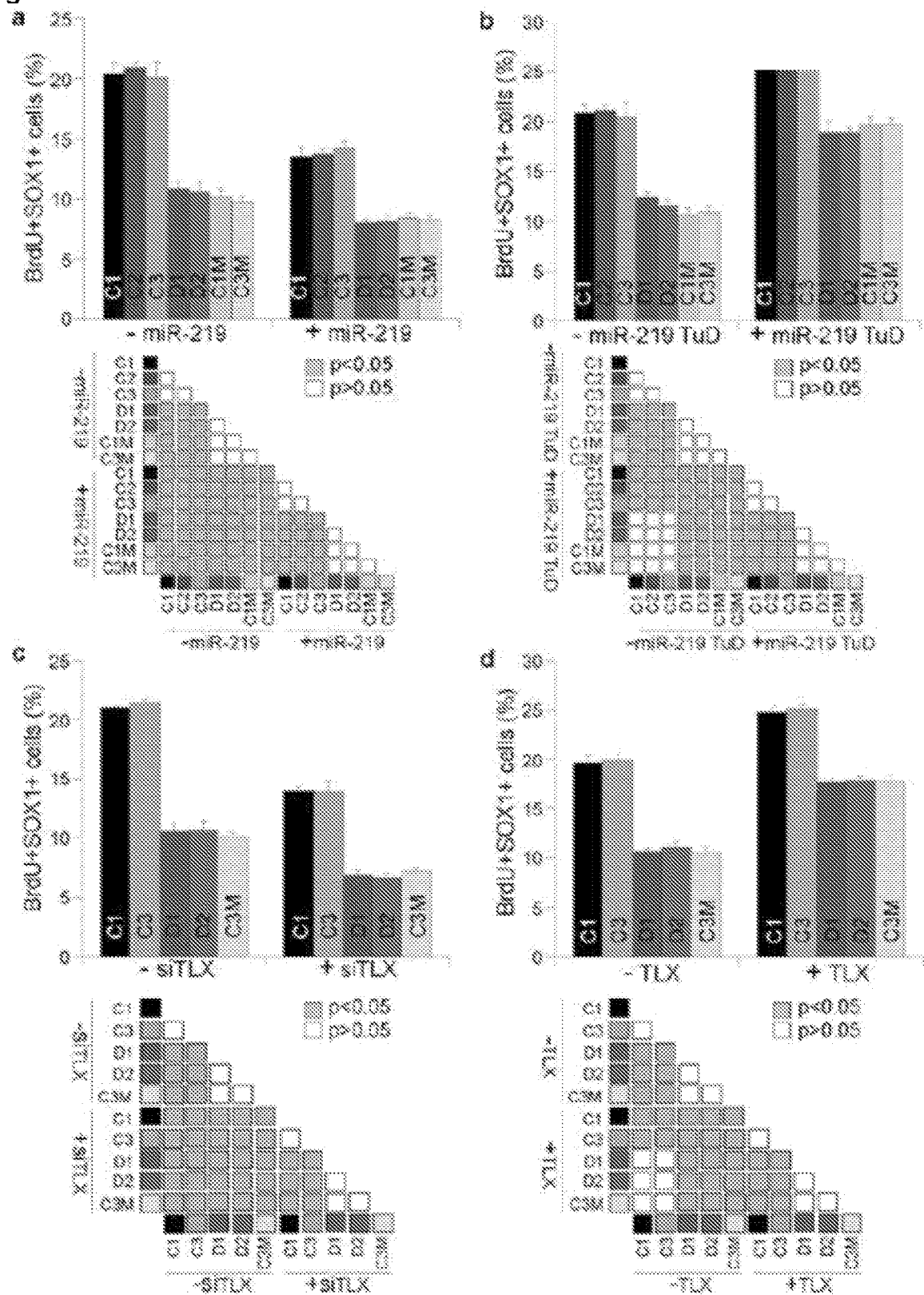

FIGS. 8a-8d illustrate that inhibition of miR-219 or overexpression of TLX rescues reduced cell proliferation in SCZ NSCs. FIG. 8a shows overexpression of miR-219 inhibited cell proliferation in WT NSCs. WT (C1, C2, C3) and DISC1-mutant NSCs (D1, D2, C1M, C3M) were transduced with virus expressing a control vector (-miR-219) or miR-219-expresing vector (+miR-219). NSC proliferation rate was determined by the percentage of BrdU+SOX1+ cells. FIG. 8b shows TuD-miR-219 rescued the proliferative defect in DISC1 mutant NSCs. WT and DISC1-mutant NSCs were transduced with a control vector (-miR-219-TuD) or TuD-miR-219-expressing vector (+miR-219-TuD). NSC proliferation rate was determined by the percentage of BrdU+SOX1+ cells. FIG. 8c shows knockdown of TLX inhibited cell proliferation in WT NSCs. WT (C1, C3) and DISC1-mutant NSCs (D1, D2, C3M) were transduced with virus expressing a control RNA (-siTLX) or TLX siRNA (+siTLX). NSC proliferation rate was determined by the percentage of BrdU+SOX1+ cells. FIG. 8d shows overexpression of TLX rescued the proliferative defect in DISC1 mutant NSCs. WT and DISC1-mutant NSCs were transduced with control vector (−TLX) or TLX-expressing vector (+TLX). NSC proliferation rate was determined by the percentage of BrdU+SOX1+ cells. n=5 for panels a & b, and n=4 for panels c & d. N represents experimental repeats. ANOVA test result was shown below each graph.

Figure 9:
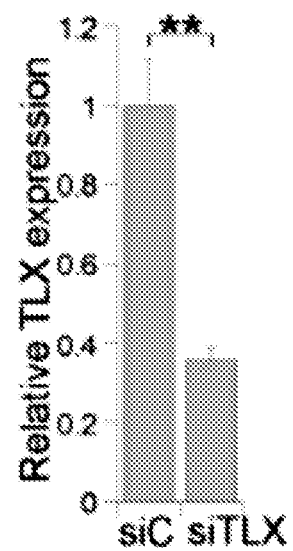

FIG. 9 shows the knockdown of TLX expression in NSCs. Mouse NSCs were transduced with lentivirus expressing a scrambled control RNA (siC) or TLX siRNA (siTLX). The expression of TLX was determined by RT-PCR. Error bars are sd of the mean for all the quantification in this study. n=5. **$p<0.01$ by student's t-test.

Figure 10:
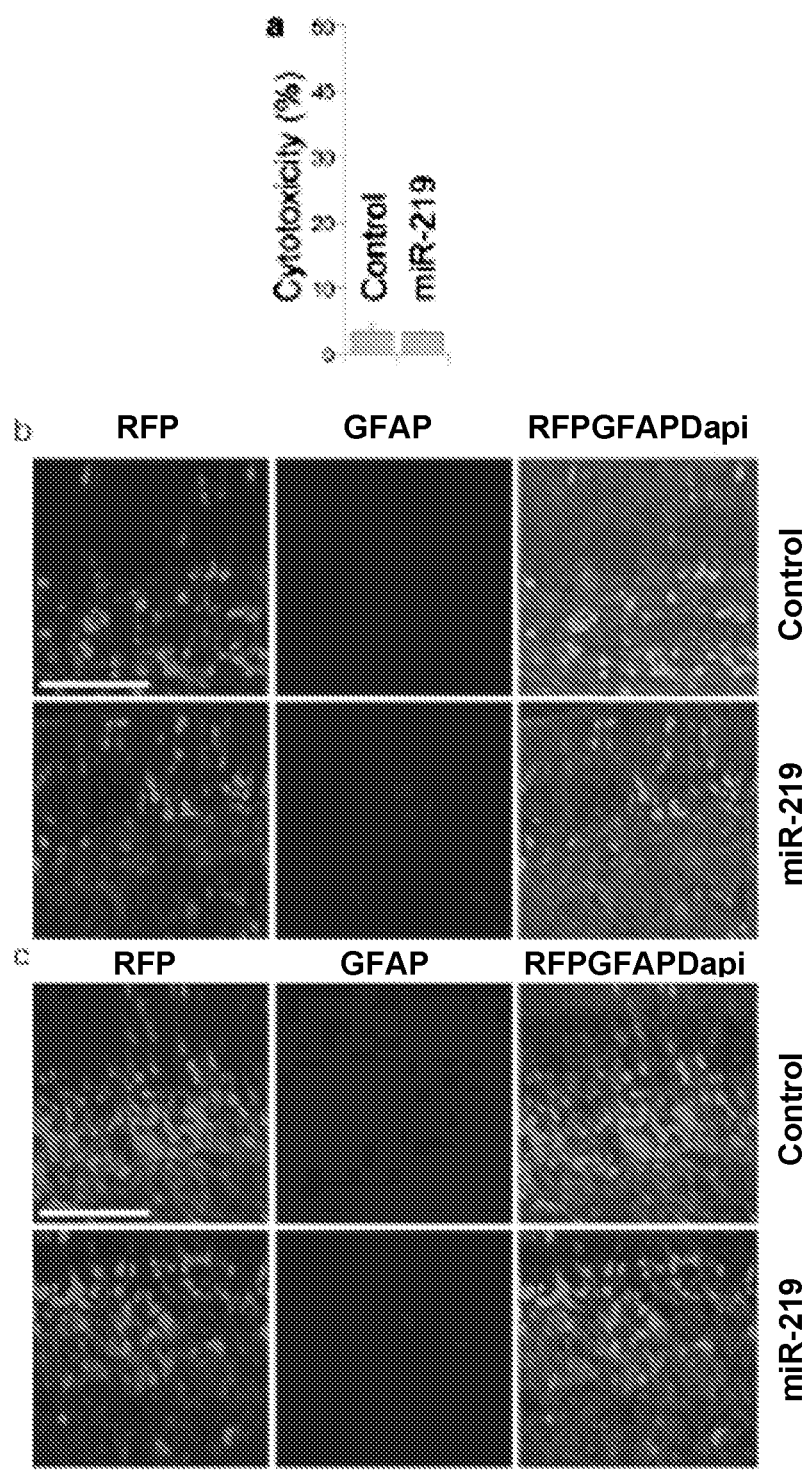

FIGS. 10a-10c illustrate the lack of toxicity and gliogenic induction in miR-219-transfected cells. FIG. 10a shows minimal cytotoxicity in miR-219-transfected NSCs. Cytotoxicity was expressed as the percent of lactate dehydrogenase (LDH) release into the medium out of the total LDH activity. n=5. FIGS. 10b and 10c show no induction of GFAP and MBP expression in miR-219-electroporated mouse brains at E15.5. Scale bar: 100 µm.

Figure 11:
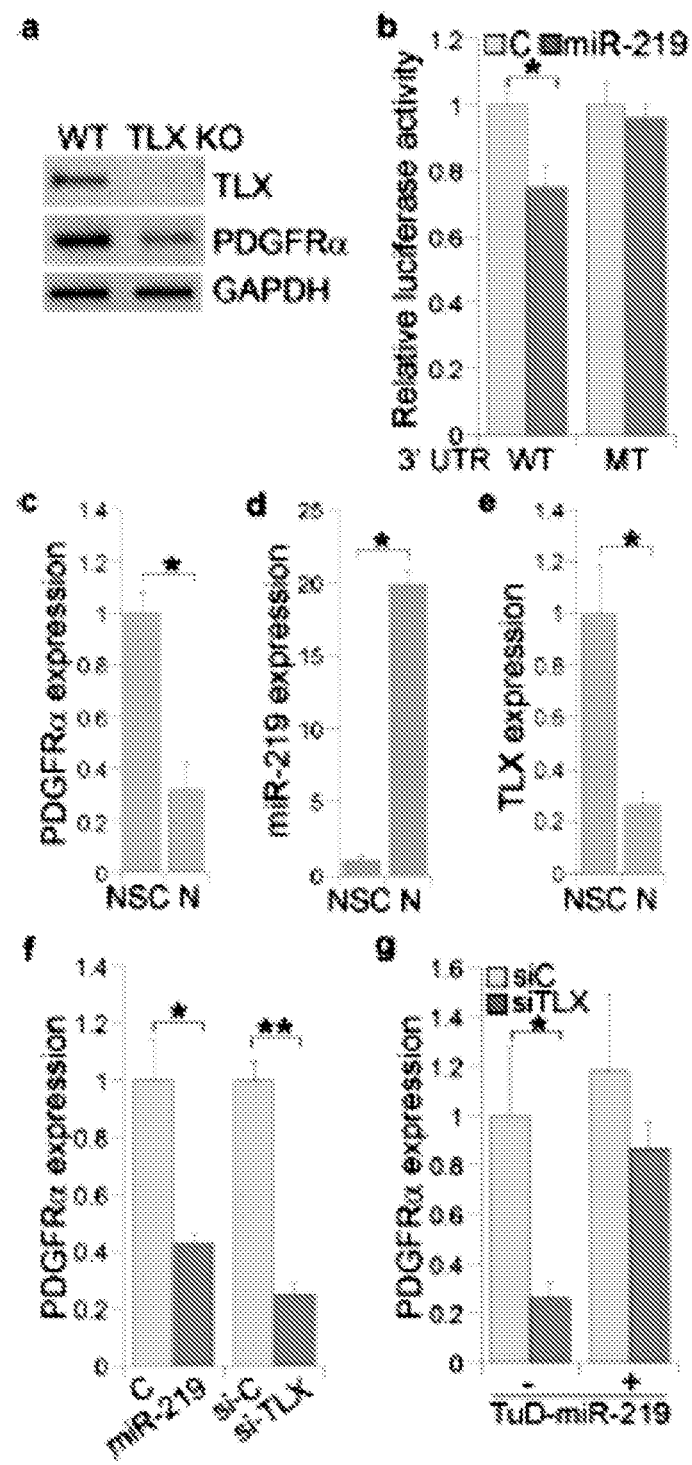

FIGS. 11a-11g illustrate that TLX-miR-219 regulates the expression of PDGFRα in NSCs. FIG. 11a shows PDGFRα expression was reduced in TLX KO mouse brains. The expression of PDGFRα in WT and TLX KO mouse brains was examined by RT-PCR. GAPDH was included as a loading control. FIG. 11b shows miR-219 represses PDGFRα 3' UTR reporter with wild type (WT), but not mutant (MT) miR-219 recognition sites. n=3. *$p<0.01$ by student's t test. FIGS. 11c-11e show the expression pattern of miR-219 in NSCs and neurons inversely correlates with that of PDGFRα and TLX. The expression levels of PDGFRα (FIG. 11c), miR-219 (FIG. 11d) and TLX (FIG. 11e) in NSCs and cortical neurons (N) derived from embryonic mouse brains were determined by RT-PCR. n=3 and *$p<0.001$ by student's t test for panels c-e. FIG. 11f shows the expression of PDGFRα is decreased in NSCs transfected with miR-219 or TLX siRNA as shown by RT-PCR analysis. n=5. *$p<0.01$, **$p<0.001$ by student's t test. FIG. 11g shows inhibition of PDGFRα expression by TLX siRNA could be rescued by the miR-219 decoy inhibitor, TuD-miR-219. The expression of PDGFRα in NSCs transduced with scramble control RNA (siC) or TLX siRNA (si-TLX), in the absence or presence of TuD-miR-219, was examined by RT-PCR. n=5. *$p<0.01$ by student's t test.

Figure 12:
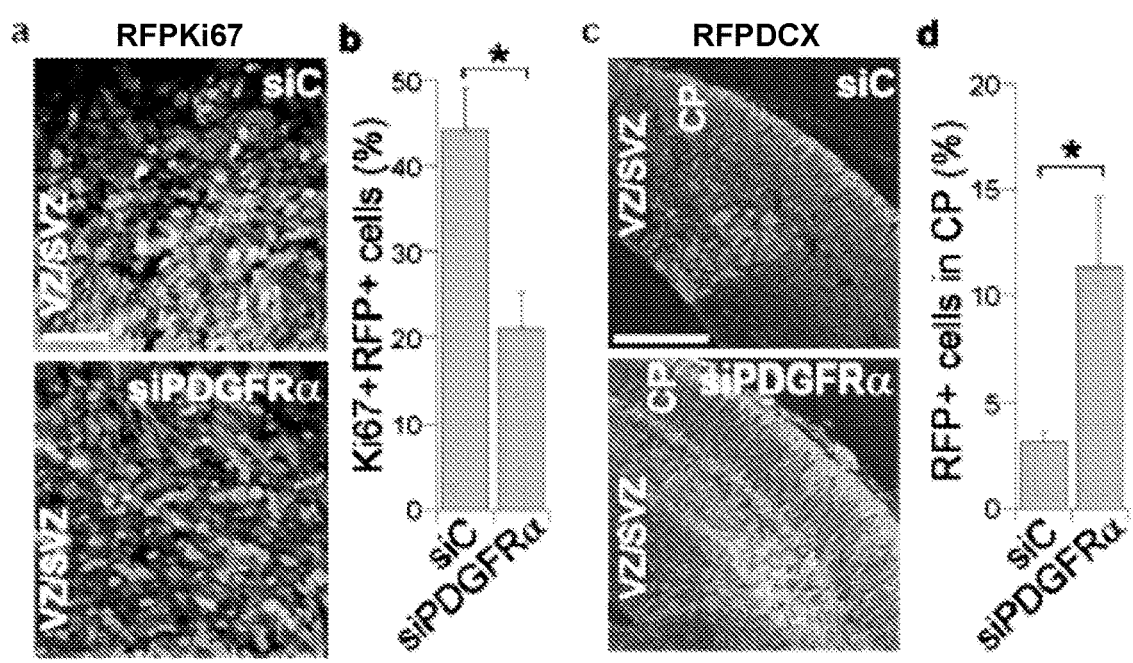

FIGS. 12a-12d illustrate that knockdown of PDGFRα inhibits NSC proliferation & promotes neuronal differentiation and migration in embryonic mouse brains. FIG. 12a shows electroporation of PDGFRα siRNA decreased NSC proliferation in the VZ/SVZ of embryonic mouse brains. The electroporated cells were labeled with RFP and proliferating cells were labeled with Ki67. FIG. 12b shows the percentage of RFP+Ki67+ cells out of total RFP+ cells in control RNA (siC) or PDGFRα siRNA (siPDGFRα)-electroporated brains is shown. n=3. *$p<0.05$ by student's t-test. FIG. 12c shows electroporation of PDGFRα siRNA led to precocious outward cell migration. The electroporated brains were labeled by RFP and stained for the neuronal marker doublecortin (DCX). FIG. 12d shows the percentage of electroporated cells (RFP+) that migrated to the CP in siC and siPDGFRα-electroporated brains. n=3. *$p<0.05$ by student's t test. Scale bar: 50 µm for panel a; 200 µm for panel c.

Figure 13:
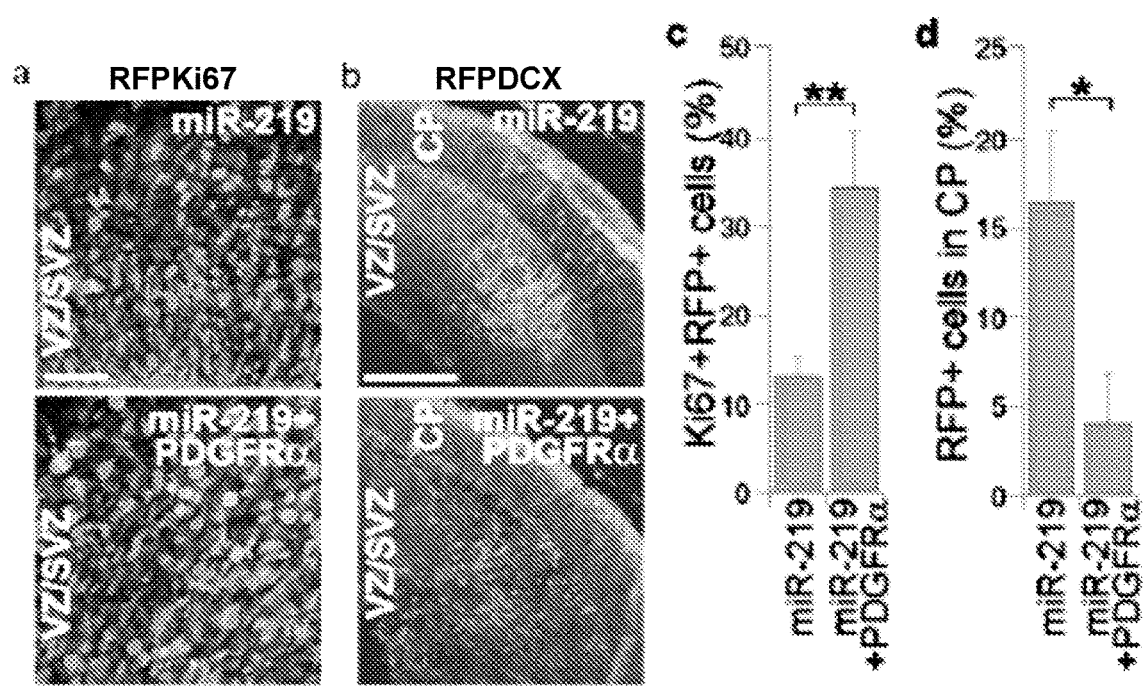

FIGS. 13a-13d illustrate that PDGFRα functions downstream of miR-219 in embryonic mouse brains. FIG. 13a shows co-electroporation with PDGFRα and miR-219 reversed the decrease in NSC proliferation induced by miR-219 in the VZ/SVZ of embryonic mouse brains. The electroporated cells were labeled with RFP and proliferating cells were labeled with Ki67. FIG. 13b shows co-electroporation with PDGFRα and miR-219 reversed precocious outward cell migration induced by electroporation with miR-219 alone. FIGS. 13c and 13d show the percentage of RFP+Ki67+ cells (FIG. 13c) or cells migrated to the CP (FIG. 13d) out of total RFP+cells in miR-219 or miR-219 and PDGFRα-electroporated brains is shown. n=3 for panels c & d. *$p<0.05$, **$p<0.01$ by student's t-test. Scale bar: 50 µm for panel a; 200 µm for panel b.

Figure 14:
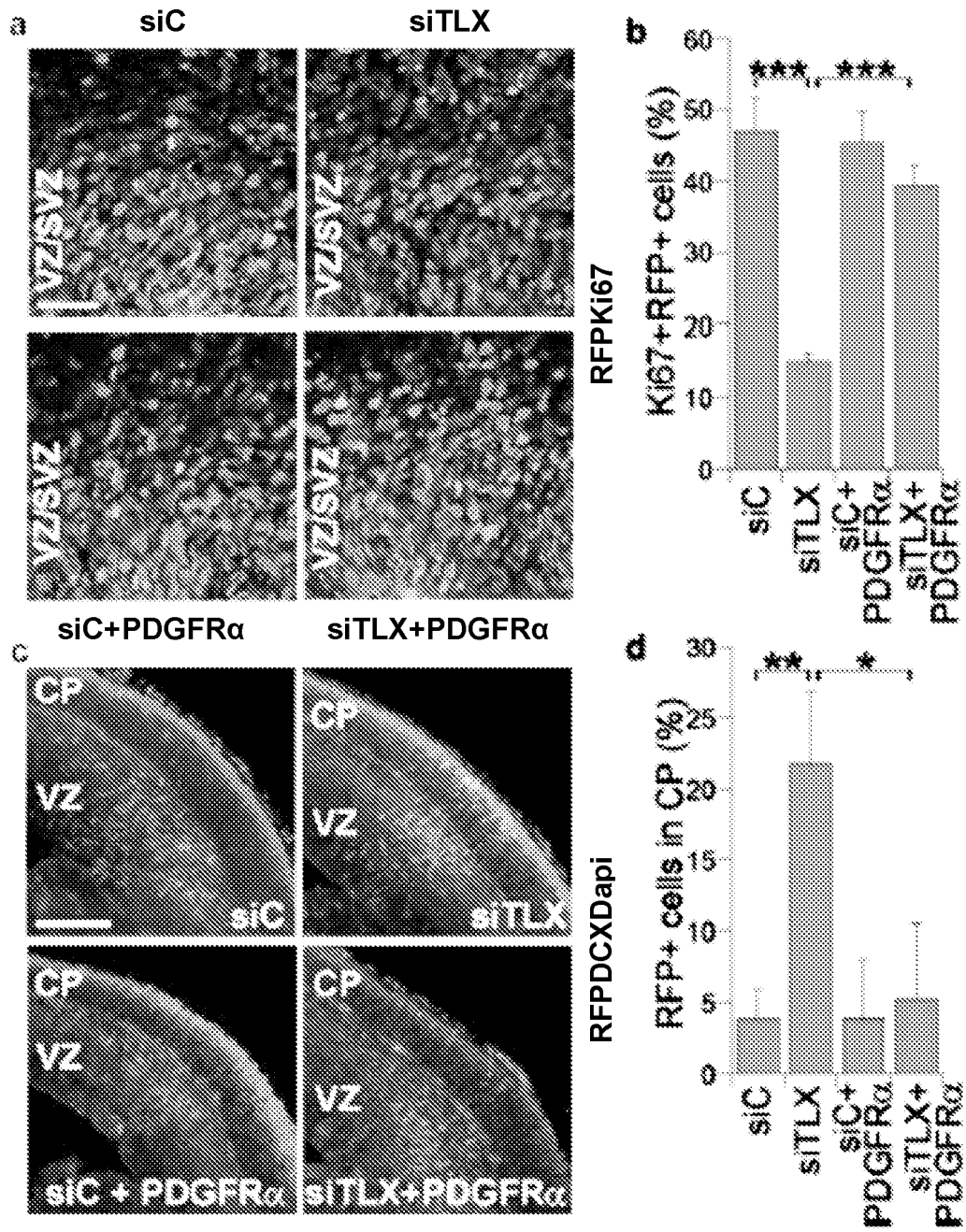

FIGS. 14a-14d illustrate that PDGFRα functions downstream of TLX in embryonic mouse brains. FIG. 14a shows co-electroporation with PDGFRα and TLX siRNA (siTLX+PDGFRα) reversed the decrease in NSC proliferation in the VZ/SVZ induced by TLX siRNA alone. A control RNA (siC) was included as a negative control for TLX siRNA. FIG. 14b shows the percentage of RFP+Ki67+ cells out of total RFP+ cells is shown. n=3. FIG. 14c shows co-electroporation with PDGFRα and TLX siRNA reversed outward cell migration induced by TLX siRNA alone. The electroporated cells were labeled by RFP. FIG. 14d shows the percentage of RFP+ cells that migrated to the CP out of total RFP+ cells is shown. n=3. *p<0.05, p<0.01, *p<0.001 by student's t test. Scale bar: 50 μm for panel a; 200 μm for panel b.

Figure 15:
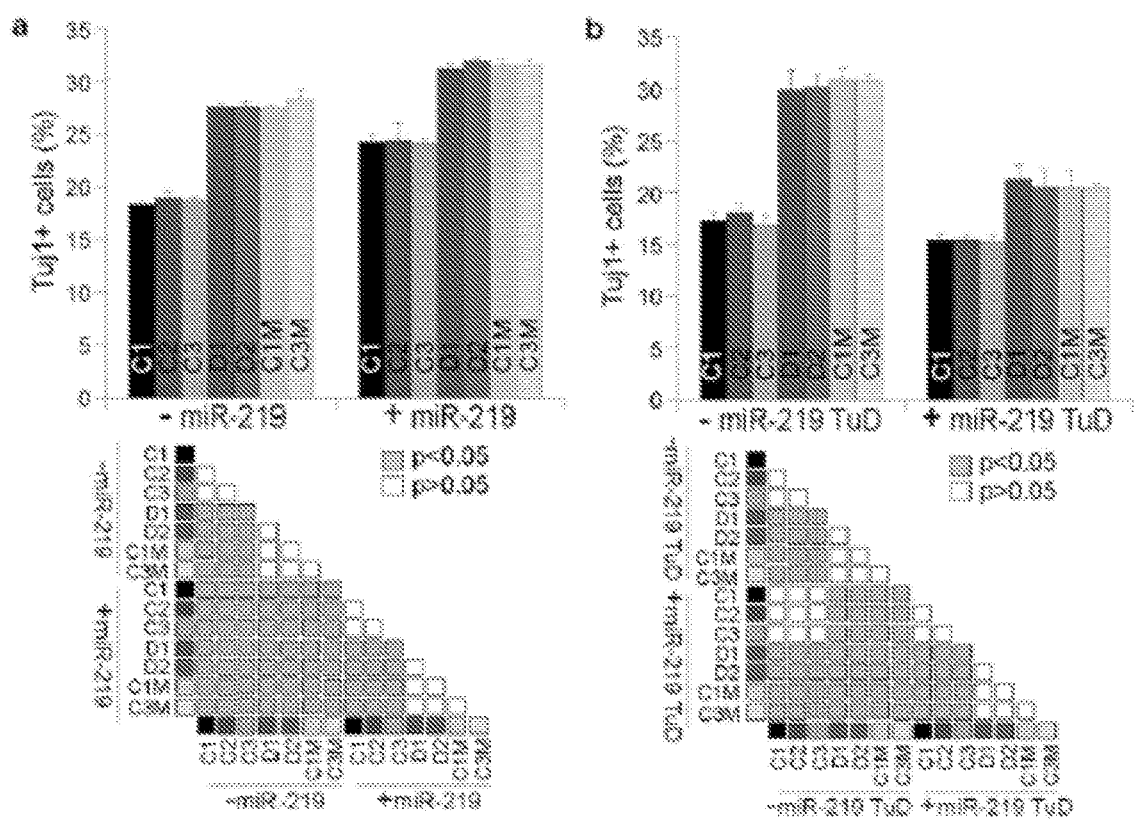

FIGS. 15a-15b show that miR-219 regulates neuronal differentiation in SCZ NSCs. FIG. 15a shows overexpression of miR-219 promotes neuronal differentiation in WT NSCs. WT (C1, C2, C3) and DISC1-mutant NSCs (D1, D2, C1M, C3M) were transduced with virus expressing a control vector (-miR-219) or miR-219-expresing vector (+miR-219). Neuronal differentiation rate was determined by the percentage of Tuj1+ cells. FIG. 15b shows inhibition of miR-219 reverses precocious neuronal differentiation in SCZ NSCs. The DISC1-mutant NSCs exhibited precocious differentiation, which was reversed by TuD-miR-219. Neuronal differentiation rate was determined by the percentage of Tuj1+ cells. n=5 for panels a & b. N represents experimental repeats. ANOVA test result was shown below the graph.

FIG. 16 shows the list of Northern blot probes and RT-PCR primers (SEQ ID NOS:1-34).

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

In one embodiment, a method of correcting a defective rate of proliferation in a population of neural stem cells (NSCs) is provided. This embodiment may include a step of contacting the population of NSCs with an effective amount of an miR-219 inhibitor, an agent to increase expression or activity of TLX, or both.

The miR-219 inhibitor used in the embodiments described herein may be any suitable agent that inhibits the expression or activity of miR-219 including, but not limited to, a tough decoy RNA, an RNAi molecule (e.g., shRNA, siRNA, or any other RNA interference molecule), or an aptamer. In certain embodiments, the miR-219 inhibitor is an miR-219-5p hairpin inhibitor (Dharmacon) or TuD-miR-219 (a tough decoy RNA). TuD-miR-219 has the following sequence (SEQ ID NO:35):

5' GAC GGC GCT AGG ATC ATC AAC CTC GAG CGC TAG CAA GTA TTC TGG TCA CAG AAT ACA ACG TCG ACC ACT AGT CAA GAT GAT CCT AGC GCC GTC TTT TTT 3'

The agent to increase expression or activity of TLX may be any suitable agent including, but not limited to, an agent to chemically modify TLX or a vector expressing a gene encoding TLX. In certain embodiments, the vector expressing TLX may be a plasmid or any suitable recombinant viral vector capable of delivering a nucleotide sequence that is expressed in a cell including, but not limited to, a lentiviral vector, an adenoviral vector, an AAV vector, or any other suitable recombinant viral vector. The vectors described herein may be designed to include the nucleotide sequence of TLX, reproduced below:

Human NR2E1 (TLX) nucleotide sequence (SEQ ID NO: 36):
ATGAGCAAGCCAGCCGGATCAACAAGCCGCATTTTAGATATCCCCTGCA
AAGTGTGTGGCGACCGCAGCTCGGGGAAGCACTACGGGGTCTACGCCT
GCGACGGCTGCTCAGGTTTTTTCAAACGGAGCATCCGAAGGAATAGGAC
CTATGTCTGCAAATCTGGAAACCAGGGAGGCTGTCCGGTGGACAAGACG
CACAGAAACCAGTGCAGGGCGTGTCGGCTGAAGAAGTGTTTGGAAGTCA
ACATGAACAAAGACGCCGTGCAGCACGAGCGGGGGCCTCGGACGTCCA
CCATCCGCAAGCAAGTGGCCCTCTACTTCCGTGGACACAAGGAGGAGAA
CGGGGCCGCCGCGCACTTTCCCTCGGCGGCGCTCCCTGCGCCGGCCTT
CTTCACCGCGGTCACGCAGCTGGAGCCGCACGGCCTGGAGCTGGCCGC
GGTGTCCACCACTCCAGAGCGGCAGACCCTCGTGAGCCTGGCTCAGCC
CACGCCCAAGTACCCCCATGAAGTGAATGGGACCCCAATGTATCTCTAT
GAAGTGGCCACGGAGTCGGTGTGTGAATCAGCTGCCAGACTTCTCTTCA
TGAGCATCAAGTGGGCTAAGAGTGTGCCAGCCTTCTCCACGCTGTCTTT
GCAAGACCAGCTGATGCTTTTGGAAGATGCTTGGAGAGAACTGTTTGTTC
TAGGAATAGCACAATGGGCCATTCCGGTTGATGCTAACACTCTACTGGCT
GTATCTGGCATGAACGGTGACAACACAGATTCCCAGAAGCTGAACAAGA
TCATATCTGAAATACAGGCTTTACAAGAGGTGGTGGCTCGATTTAGACAA
CTCCGGTTAGATGCTACTGAATTTGCCTGTCTAAAATGCATCGTCACTTT
CAAAGCCGTTCCTACACATAGTGGTTCTGAACTGAGAAGTTTCCGGAATG
CTGCCGCCATTGCAGCCCTTCAAGATGAGGCTCAGCTAACGCTCAACAG
CTACATCCATACCAGATATCCCACTCAACCCTGTCGCTTTGGAAAACTCC
TGTTGCTTTTGCCAGCTTTACGTTCTATTAGCCCATCAACTATAGAAGAA
GTGTTTTTCAAAAAAACCATCGGCAATGTGCCAATTACAAGACTGCTTTC
AGATATGTACAAATCCAGTGATATCTAA When delivered to a target cell such as a neural stem cell using the vector, the nucleotide sequence above is translated to express the TLX protein, the amino acid sequence of which is shown below:

Human NR2E1 (TLX) amino acid sequence (SEQ ID NO: 37):
MSKPAGSTSRILDIPCKVCGDRSSGKHYGVYACDGCSGFFKRSIRRNRTY
VCKSGNQGGCPVDKTHRNQCRACRLKKCLEVNMNKDAVQHERGPRTSTIR
KQVALYFRGHKEENGAAAHFPSAALPAPAFFTAVTQLEPHGLELAAVSTT
PERQTLVSLAQPTPKYPHEVNGTPMYLYEVATESVCESAARLLFMSIKWA
KSVPAFSTLSLQDQLMLLEDAWRELFVLGIAQWAIPVDANTLLAVSGMNG
DNTDSQKLNKIISEIQALQEVVARFRQLRLDATEFACLKCIVTFKAVPTH
SGSELRSFRNAAAIAALQDEAQLTLNSYIHTRYPTQPCRFGKLLLLLPAL
RSISPSTIEEVFFKKTIGNVPITRLLSDMYKSSDI In another embodiment, a portion of TLX may be used as the agent to increase expression or activity of TLX, such as the Dpi domain of TLX. The Dpi domain may be expressed by the vector or delivered to the population of NSCs. The nucleotide and amino acid sequences of Dpi are shown below:

Human TLX DPI nucleotide coding sequence (1021 to
1077 nt) (SEQ ID NO: 38):
GGAAAACTCCTGTTGCTTTTGCCAGCTTTACGTTCTATTAGCCCATCAA
CTATAGAA Human TLX DPI amino acid sequence (341 aa to 359
aa) (SEQ ID NO: 39):
GKLLLLLPALRSISPSTIE The mir-219 inhibitor, the agent to increase expression or activity of TLX, or both may be used to contact the population of NSCs in vitro. In this case, the population of in vitro cells are derived from a subject suffering from a neurodevelopmental disorder such as schizophrenia, bipolar disorder, or depression.

Alternatively, the agent to increase expression or activity of TLX, or both may be used to contact the population of NSCs in vivo. In this case, the population of in vivo cells are present in the nervous system of a subject suffering from schizophrenia, bipolar disorder, or depression.

As discussed in the examples below, the mir-219 inhibitor, the agent to increase expression or activity of TLX, or both causes an increase in NSC proliferation rate, and can therefore be used in methods for treating neurodevelopmental disorders that are associated with having a defective proliferation rate of NSCs, such as schizophrenia, bipolar disorder, or depression. The mir-219 inhibitor, the agent to increase expression or activity of TLX may be used separately or in combination to increase proliferation of NSCs in a subject suffering from one of these disorders.

The terms "treat," "treating," or "treatment" as used herein with regards to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. In some embodiments, treating a condition means that the condition is cured without recurrence.

The phrase "a therapeutically effective amount," "therapeutically effective dose" or "an effective amount" as used herein refers to an amount of an agent, including a nucleic acid, a peptide, or a chemical compound, or a composition that produces a desired therapeutic effect. The precise therapeutically effective amount is an amount of the agent or composition that will yield the most effective results in terms of efficacy in a given subject. This amount will vary depending upon a variety of factors, including but not limited to the characteristics of the agent or composition (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of an agent, population of cells, or composition and adjusting the dosage accordingly. For additional guidance, see Remington: The Science and Practice of Pharmacy (Gennaro ed. $20^{th}$ edition, Williams & Wilkins PA, USA) (2000).

It is within the purview of one of ordinary skill in the art to select a suitable route of administration of the pharmaceutical compositions disclosed herein. For example, these pharmaceutical compositions can be administered by oral administration including sublingual and buccal administration, and parenteral administration including intravenous administration, intramuscular administration, and subcutaneous administration. In certain embodiments the pharmaceutical composition is administered through an intrathecal or intracranial route of administration.

Also disclosed herein are methods of treating a neurodevelopmental disorder in a subject. The subject may be suffering from schizophrenia, bipolar disorder, or depression. According to the embodiments described herein, the methods may include administering a therapeutically effective dose of a pharmaceutical composition to the subject. In certain embodiments, the pharmaceutical composition may include (i) an agent to increase expression or activity of TLX, (ii) an miR-219 inhibitor, or both (i) and (ii). As disclosed herein, increasing expression or activity of TLX may maintain normal NSC proliferation in the subject. In certain embodiments, the agent may be a vector expressing a gene encoding TLX. In embodiments where the pharmaceutical composition comprises an agent to increase expression or activity of TLX, the pharmaceutical composition may further comprise an miR-219 inhibitor. In embodiments where the pharmaceutical composition comprises an miR-219 inhibitor, the pharmaceutical composition may further comprise an agent to increase expression or activity of TLX. In other embodiments where the pharmaceutical composition comprises an agent to increase expression or activity of TLX, the methods may further include administering a therapeutically effective dose of a second pharmaceutical composition to the subject, the pharmaceutical composition comprising an miR-219 inhibitor. In other embodiments where the pharmaceutical composition comprises an miR-219 inhibitor, the methods may further include administering a therapeutically effective dose of a second pharmaceutical composition to the subject, the pharmaceutical composition comprising an agent to increase expression or activity of TLX. As disclosed herein, the miR-219 inhibitor may be a tough decoy RNA, an RNAi molecule, or an aptamer. In certain embodiments, the miR-219 inhibitor may be an miR-219-5p hairpin inhibitor or TuD-miR-219.

Expression of miR-219 may also be used as a biomarker to detect schizophrenia, bipolar disorder, or depression. In certain embodiments, the miR-219 may be detected in exosomes or cerebrospinal fluid (CSF).

In this disclosure, a role for miR-219 in the regulation of mammalian NSC proliferation and differentiation is demonstrated, and TLX is identified as an upstream regulator of miR-219. Moreover, p68, Drosha and DGCR8 are identified as novel TLX-interacting molecules, and an unexpected role for TLX in regulating miRNA processing at the post-transcriptional level is uncovered. Furthermore, miR-219 expression is up-regulated, whereas TLX expression is down-regulated in SCZ NSCs. Overexpression of TLX or an miR-219 inhibitor is able to rescue the proliferative defects in SCZ NSCs.

In this disclosure, it has been demonstrated that TLX regulates miRNA processing independent of its well-characterized role in transcriptional regulation, and that miR-219 acts downstream of TLX to regulate NSC proliferation and differentiation in mammalian brains. Moreover, miR-219 expression is elevated, whereas TLX expression is reduced, in DISC1-mutant SCZ patient iPSC-derived NSCs. Overexpression of TLX or inhibition of miR-219 could rescue the reduced cell proliferation in DISC1-mutant SCZ NSCs.

Disclosed herein is an unexpected role for TLX in miRNA maturation at the post-transcriptional level beyond transcriptional regulation. In an unbiased search for TLX-interacting proteins, the RNA helicase p68, a component of the miRNA processing machinery, was identified as a novel TLX-interacting protein. Further study revealed that TLX also interacts with p68-associated Drosha and DGCR8, the two main components of miRNA processing machinery. It is shown in this disclosure that TLX inhibits miR-219 processing by interacting with the p68/Drosha/DGCR8 complex, which in turn prevents the miRNA processing machinery from binding to miR-219 primary form. Either knockdown of TLX or blocking the interaction between TLX and the miRNA processing machinery resulted in potent induction of pre-miR-219 and mature miR-219 expression, but had minimal effect on pri-miR-219 expression. The concept that a transcription factor like TLX can participate in post-transcriptional regulation of gene expression may serve as a general paradigm for many of these classes of cellular factors to control cell fate determination.

Robust inhibition of cell proliferation and induction of neuronal differentiation were detected when miR-219 was overexpressed in NSCs. However, no obvious change in cell proliferation and differentiation was observed in NSCs treated with miR-219 inhibitor, presumably because the basal miR-219 expression level is low in NSCs. In TLX siRNA-treated NSCs, where miR-219 expression level was elevated, inhibition of miR-219 was able to rescue the proliferative defect and precocious differentiation. It is also possible that the action of other miRNAs, such as miR-9, miR-124, miR-137, miR-338, or let-7, could compensate for miR-219 inhibition in NSCs. miR-219 has been shown to induce oligodendrocyte differentiation in electroporated mouse brains that were harvested at E17.5 [27]. However, the induction of oligodendrocyte marker expression in miR-219-electroporated mouse brains harvested at E15.5 was not detected, presumably because brains were harvested at an earlier stage that is active for neurogenesis but not for gliogenesis yet. It is possible that miR-219 could play distinct roles at different developmental stages.

miR-219 is dysregulated in neurodevelopmental disorders, including SCZ, bipolar disorder and depression [29, 32,42,43]. Understanding the regulation of miR-219 expression in mammalian brains will not only broaden the knowledge about neurodevelopment, but also provide insights into the pathogenesis of neurological disorders. It is shown in this disclosure that TLX represses miR-219 biogenesis in NSCs during mouse brain development. PDGFRα was also identified as a downstream target of the TLX-miR-219 cascade in NSCs. PDGFRα has been shown to be expressed in oligodendrocyte progenitor cells [44] and play a role in oligodendrocyte differentiation downstream of miR-219 [26]. It is shown in this disclosure that knockdown of PDGFRα expression induced NSC phenotypes similar to that induced by miR-219 overexpression, whereas overexpression of PDGFRα restored NSC phenotypes induced by miR-219 overexpression or TLX siRNA treatment.

DISC1 is required for mouse NSC proliferation [40]. However, little is known about its function in human NSCs. In this disclosure, DISC1 has been found to play a role in regulating human NSC proliferation by studying NSCs derived from D/SCI-mutant SCZ patient iPSCs and genetically engineering isogenic iPSCs with an introduced DISC1 mutation. The observation that miR-219 expression is up-regulated, whereas TLX expression is down-regulated, in D/SCI-mutant NSCs provides a direct link between TLX and miR-219 expression and DISC1 function. Previous studies have shown that TLX KO mice exhibit neuroanatomical and behavioral abnormalities similar to that in D/SCI-mutant mice and SCZ patients, including increased lateral ventricles, reduced cerebral cortex, reduced neurogenesis and memory, and increased anxiety and hyperactivity [2,3,6,7,45-56]. The finding of altered expression of TLX in DISC1-mutant NSCs suggests that mutant DISC1 could regulate TLX expression, which in turn induces abnormal miR-219 expression and inhibition of NSC proliferation.

SCZ is a neurodevelopmental disorder for which the pathological mechanism remains elusive. Increasing evidence suggests that miRNAs may play important roles in the etiology of SCZ [57]. miRNA-219 is highly up-regulated in the prefrontal cortex of SCZ patients [29,32] and mediates the behavioral effects of the NMDA receptor antagonist Dizocilpine [58]. However, whether miR-219 plays a role in SCZ pathogenesis remained unknown. This disclosure has identified a novel role for miR-219 in SCZ NSCs; elevated miR-219 expression reduces SCZ NSC proliferation.

Multiple studies provide evidence that NSC proliferation and neurogenesis are tightly linked to SCZ pathogenesis [39,59,60]. Recent studies using patient iPSCs have identified phenotypic differences in human iPSC-derived neural progenitor cells [61] and provided insights into how risk factors for SCZ regulate NSC phenotypes and neurodevelopment [62]. In this disclosure, a direct link between DISC1 mutation and altered TLX and miR-219 expression, and a causative link between dysregulated TLX and miR-219 expression and proliferative defects in DISC1-mutant SCZ NSCs are identified. Disclosed herein is a molecular mechanism underlying defective NSC proliferation in SCZ. Moreover, both TLX and miR-219 could be potential therapeutic targets for SCZ and that TLX inducers or miR-219 inhibitors may serve as potential therapeutic tools to maintain normal NSC proliferation in SCZ patients.

The working examples below further illustrate various embodiments of this disclosure. By no means the working examples limit the scope of this invention.

EXAMPLE 1

Materials and Methods

Animals. Female ICR or Swiss Webster mice at gestation 13.5 were used for in utero electroportion experiments. All mice were produced in the Animal Resource Core of City of Hope. All animal-related work was performed under the IACUC protocol 03038 approved by City of Hope Institutional Animal Care and Use Committee. Mice were maintained in a 12 hr light:12 hr dark light cycle at 4 mice per cage.

Antibodies and immunostaining. Antibodies were used to Flag epitope tag M2 (Sigma, F2426 for IP), HA (1:500, Santa Cruz, sc-805), p68 (1:1000, Abcam, ab10261), Drosha (1:1000, cell signaling, #3364), DGCR8 (1:500, Protein Tech Group, Inc, 10996-1-AP), BrdU (1:5000, Accurate, OBT0030CX), DCX (1:300, Santa Cruz, sc-8806) and Ki67 (1:200, GeneTex, GTX16667). Immunostaining of embryonic mouse brains was performed using antibodies for DCX and Ki67. For Ki67 staining, antigen retrieval was performed by incubating slides in sodium citrate buffer (10 mM sodium citrate, pH 6.0 and 0.1% Triton X) at 80° C. for 10 min before staining.

Mouse NSC culture. Embryonic mouse NSCs were prepared using an established protocol [63] as follows. E14.5 mouse brains were dissociated by gentle pipetting. The dissociated cells were seeded on polyornithine- and fibronectin-coated plates and cultured in N2 medium (DMEM F12, 25 μg per ml insulin, 100 ng per ml apotransferrin, 30 nM sodium selenite, 20 nM progesterone and 100 µM putrescine) supplemented with 10 ng per ml FGF2. Cells were maintained as mycoplasm-free culture as revealed by routine mycoplasm screen using MycoAlert Mycoplasma Detection Kit. For differentiation, NSCs were dissociated into single cells and cultured in N2 medium supplemented with 0.5% fetal bovine serum and 10 µM Forskolin for 5 days. For BrdU labeling, 10 µM BrdU was added to NSCs and pulsed for 30 min. Cells were then fixed and acid treated, followed by immunostaining with anti-BrdU antibody. Transfection of NSCs with reporter plasmid DNA, miRNA or siRNA was performed using TransFectin (BioRad), following manufacturer's instructions. For actinomycin D treatment, control or TLX siRNA-transduced NSCs were treated with 1 µM actinomycin D for 3 hr, followed by cell harvesting and RNA isolation.

Plasmid DNAs. pCK-Flag-Drosha [64] and pCK-Flag-DGCR8 [64] were gifts from Dr. V. N. Kim. To prepare the PDGFRα 3' UTR reporter construct, DNA fragments containing mouse PDGFRα 3' UTR were subcloned into psi-CHECK vector (Promega). The miR-219-5P target site 5'-GACAATCA-3' (SEQ ID NO: 40) in PDGFRα 3' UTR was mutated into 5'-GATCGTCA-3' (SEQ ID NO: 41) by site-directed mutagenesis. The cDNA of mouse PDGFRα was purchased from ATCC and subcloned into pEF-pUb-RFP vector [4]. To make TLX siRNA or scrambled control RNA-expressing lentiviral vector, DNA fragments containing TLX siRNA or scrambled control siRNA hairpin sequences were subcloned into pHIV-GFP vector [65]. To prepare the Dpi peptide or control peptide-expressing vector, DNA fragment containing the Dpi (amino acid residues 341-359) (SEQ ID NO: 42) or control peptide (amino acid residues 201-223) (SEQ ID NO: 43) of TLX was fused in frame to three copies of nuclear localization signals and cloned into the CMX-HA or CSC-GFP vector [3]. To make miR-219-expressing retroviral vector, DNA oligos of miR-219 were annealed and cloned into the UEG vector [66]. To prepare the construct of TuD-miR-219, DNA oligos of TuD-miR-219, 5'-TCG AAG AAT TGC GTT CTG ATG GAC AAT CA-3' (SEQ ID NO: 44) and 5'-CTA GTG ATT GTC CAT CAG AAC GCA ATT CT-3' (SEQ ID NO: 45) were annealed and cloned into the U6-TuD vector. The DNA fragment containing the U6 promoter and TuD-miR-219 was then subcloned into pHIV-GFP vector or CMVLV lentiviral vector containing a puromycin-resistant gene [65]. To prepare miR-219-Glo vector, 392 bp fragment of pri-miR-219 including the pre-miR-219 hairpin loop was PCR amplified using the following primers: 5'-TTC ATA GAG CTC ACA CCG GCT TGT CCA CCT TAC-3' (SEQ ID NO: 46) and 5'-TTC ATA CTC GAG GAG GAT ACG GAA AGA GGC GAG-3' (SEQ ID NO: 47). The PCR product was digested with SacI and XhoI site and cloned into the pmirGLO vector (Promega). To prepare miR-1224-Glo vector, 398 bp fragment of pri-miR-1224 was PCR amplified using the following primers: 5'-GAT AGC TAG CAA TGG CAA CTC CAA GCG TGC T-3' (SEQ ID NO: 48) and 5'-ATG AGG CCG AGG TGG GGC TGA GTC TAG AGA TC-3' (SEQ ID NO: 49). The PCR product was digested with NheI and XbaI and cloned into the pmirGLO vector (Promega).

siRNAs and miRNAs. All synthetic siRNAs, miRNAs and their controls were purchased from Dharmacon. The ON-TARGET plus siRNA for TLX (J-065577-12-0005) and non-targeting control siRNA (D-001810-01-05) were used for the experiments of TLX knockdown; the ON-TARGET plus SMARTpool siRNA for PDGFRα (L-048730-00-0005) and control siRNA pool (D-001810-10-05) were used for the experiments of PDGFRα knockdown. The miRIDIAN miRNA mimic for miR-219-5p (c-310578-05-0005), negative control (CN-001000-01-05), and miR-219-5p hairpin inhibitor (IH-310578-07-0005) were used for overexpressing miR-219 or inhibiting miR-219 action in mouse NSCs.

Northern blot analysis and RT-PCR. Total RNAs from tissue cultured cells or 6 to 8-week-old WT or TLX KO mouse brains were isolated using TRizol (Invitrogen) in accordance with manufacturer's instructions. Oligonucleotides complementary to miRNA sequences were end-labeled with $\gamma^{32}$P-ATP and used as probes for Northern blot analysis. The sequences for the probes are listed in FIG. 16. RT-PCR was performed to detect the levels of primary, precursor and mature miR-219, or TLX and PDGFRα mRNAs. Reverse transcription was performed using Tetro cDNA synthesis kit (Bioline) and the expression levels of pri-miRNA and pre-miRNA of miR-219, and TLX and PDGFRα mRNAs were determined using DyNAmo Flash SYBR Green qPCR mix (Thermoscientific) and StepOnePlus Real-Time PCR system (Applied Biosystems). For detection of the mature miR-219, TaqMan MicroRNA assay kit (Applied Biosystems) was used according to manufacturer's protocol. Data analysis was done by Comparative Ct method. Results were normalized to β-actin for pri-miRNA, pre-miRNA, TLX and PDGFRα mRNAs, and snoRNA or U6 for mature miRNA. The primers are listed in FIG. 16.

In vivo monitoring of pri-miRNA processing. The miR-219-Glo, miR-1224-Glo or control-Glo (pmirGLO, Promega) vector was transfected together with TLX-expressing vector or TLX siRNA-expressing vector. The firefly luciferase activity was measured 48 hr after transfection and normalized with the Renilla luciferase internal control. The results were then normalized with the luciferase activity in cells transfected with the control vector(s).

Nuclear extract preparation and immunoprecipitation. To make stable HeLa cell line that express HA or HA-TLX, HeLa cells were transduced with lentivirus expressing HA or HA-TLX and a GFP reporter, and plated the transduced cells at 1 cell per well in a 96-well plate. The GFP-positive clones derived from single GFP-positive cells were expanded to make stable cell lines. The expression of HA-TLX in cells transduced with the HA-TLX-expressing virus was confirmed by TLX Western blot analysis. Nuclear extracts were prepared from the stable cell line expressing HA or HA-TLX following a published method [67]. Every ml of nuclear extract was pre-cleared using 20 µl of protein G and 20 µl of IgG-AC (Santa Cruz, sc-2345) for 5 hr, and then incubated with HA beads (Santa Cruz, sc-805 AC) at 4° C. for overnight. Proteins pulled down by the HA beads were collected at 8,200 g for 1 min, then washed with 500 µl TBS for 20 min twice, and re-suspended in protein loading buffer for protein gel electrophoresis and subsequent mass spectrometry analysis.

Mass spectrometry. Proteins were separated on a 4-12% Bis-Tris NuPAGE gel with MES running buffer (Novex, life technology) and stained with SimplyBlue SafeStain solution (Life Technology) to visualize the differentially expressed proteins. Corresponding protein gel bands were excised and destained in ammonium bicarbonate (100 mM)/acetonitrile (45%) followed by in-gel processing, which included reduction with tris(carboxyethyl) phosphine (10 mM), alkylation with iodoacetamide (50 mM), and digestion with sequencing grade trypsin (300 ng per band, Promega); all steps were performed in 100 mM ammonium bicarbonate, pH 7.9. Extracted peptides were acidified with formic acid (1%) and injected straightly into the liquid chromatography (LC) mass spectrometry (MS) system, consisting of a binary pump Agilent 1200 HPLC, a 6520 quadrupole time-of-flight mass spectrometer (Agilent), equipped with a chip cube ion source, utilizing a high capacity LC/MS chip (Agilent) with a 150 mm×75 µm Zorbax 300SB-C18 on-board analytical reverse phase column and a 160 nl trapping column. 10 µl sized peptide samples were loaded at 4 µl per min. LC was performed with a gradient mobile phase system containing buffer A (0.1% aqueous formic acid) and B (100% acetonitrile, 0.1% formic acid). A 50-minute gradient elution from the analytical column was conducted from 7 to 85% buffer B at 300 nl per min. MS and tandem MS analysis of peptide ions with $z>2^+$ was performed in data-dependent mode. Automated collision energy settings were set by the acquisition software, MassHunter (Agilent). The resulting data was analyzed using the GPM X! Tandem search engine (The Global Proteome Machine Organization) with the human protein database and Scaffold (Proteome Software) at a 1% false discovery rate setting.

Immunoprecipitation and Western blotting. Cells were lysed with lysis buffer containing 50 mM Tris-HCl, pH 7.8, 150 mM NaCl, 1% NP40, 0.1% deoxycholate and protease inhibitor cocktails (Roche). For DNase and RNase treatment, cell lysates were treated with 40 U per ml DNase and 10 µg per ml RNase at 37° C. for 30 min. Lysates were immunoprecipitated using anti-Flag (Sigma, F2426) or anti-HA (Santa Cruz, sc-805 AC) antibodies. For co-immunoprecipitation of endogenous proteins, E13.5 mouse brains were homogenized in the above lysis buffer. Lysates were immunoprecipitated using TLX antibody, followed by immunoblotting using indicated antibodies. To determine whether Dpi disrupts the TLX-Drosha interaction, constructs expressing Dpi (TLX residues 341-359) or a control peptide (TLX residues 201-223), together with HA-TLX and Flag-Drosha were transfected into HEK293T cells. Cell lysates were immunoprecipitated with Flag antibody (Sigma, F2426), followed by immunoblotting with anti-HA (1:500, Santa Cruz, sc-805) or anti-Flag antibody (1:500, Sigma, F1804). Images in FIGS. 1a and 1b, FIGS. 2c, 2d and 2f, and FIGS. 5b-5e have been cropped for presentation.

RNA immunoprecipitation (RIP). RIP was performed under native condition [68]. NSCs were transduced with lentivirus expressing TLX siRNA or scrambled control RNA. Cell pellets were resuspended in ice cold lysis buffer containing 100 mM KCl, 5 mM $MgCl_2$, 10 mM HEPES (pH 7.0), 0.5% NP40, 1 mM DTT, 100 U per ml RNase Inhibitor (Promega), and protease inhibitor cocktail (Roche), and lysates were passed through a 27.5 gauge needle 4 times to promote nuclear lysis. Eighty units of DNase (Ambion) was added to the lysates, which were then incubated on ice for 30 min. Cell lysates were diluted in NT2 buffer (50 mM Tris-HCl, pH 7.4, 150 mM NaCl, 1 mM $MgCl_2$, 0.05% NP40, 1 mM DTT, RNase Inhibitor and protease inhibitor cocktail) and pre-cleared with protein G agarose. One tenth volume of supernatant was saved as input. The rest of the supernatant was incubated with 5 µg of antibodies at 4° C. for overnight. After incubating with protein G agarose, the RNA-antibody complex was precipitated and washed with NT2 buffer 4 times. RNA was extracted using Trizol (Invitrogen) according to manufacturer's instructions. Reverse transcription was performed using Tetro cDNA synthesis kit (Bioline), followed by PCR reaction.

In utero electroporation. A solution including 100 µM miRNA, siRNA or miRNA inhibitor with 5 µg per µl plasmid DNA expressing RFP only or RFP and PDGFRα was electroporated into E13.5 wild type ICR mouse brains. Both male and female mice were used. For electroporation of the Dpi peptide-expressing vector, plasmids expressing Dpi and RFP or Dpi, RFP and TuD-miR-219, at 2.5 µg per µl each, were electroporated into E13.5 mouse brains. Two days later, the electroporated brains were dissected and sectioned at 20 µm thickness, followed by immunostaining.

Human iPSC culture and differentiation. Human iPSCs were maintained and cultured in Essential 8 (E8) medium (Gibco, A15169-01). For NSC differentiation, iPSCs were detached using 0.5 mM EDTA and cultured in E8 medium for 6 days in suspension for embroid body (EB) formation, then switched to neuronal induction medium (50% DMEM/F12, 50% Neurobasal, 0.5×N2, 0.5×B27, 2 mM L-Glutamine, 0.1 mM NEAA, and 100 units penicillin/streptomycin) supplemented with 5 µM SB431542 and 0.25 µM LDN for 3 days. The EB spheres were transferred into matrigel-coated plates and cultured in neuronal induction medium for 7 days. Rosette structures were mechanically lifted and cultured in neuronal induction medium supplemented with basic FGF (5 ng per ml) and EGF (20 ng per ml) for expansion. Neurospheres were stained for NSC markers using antibodies for SOX1 (1:500, Millipore, AB15766) and NESTIN (1:1000, BD, 611659). All the cells used in this study were maintained as mycoplasm-free culture as revealed by routine mycoplasm screen using MycoAlert Mycoplasma Detection Kit.

Human NSC proliferation and differentiation. Human iPSC-derived NSCs were seeded on matrigel coated 24-well plates in proliferation media and cultured for 24 hr. Lentivirus expressing miR-219 or TuD-miR-219 and a GFP reporter was added to human NSCs in 24-well plates for 16 hr. The virus-transduced cells were labeled by GFP. For proliferation assay, cells were allowed to recover for 2 days and then treated with 10 µM BrdU for 1 hr, followed by immunostaining for BrdU and SOX1. Nuclei were counterstained using DAPI. NSC proliferation rate was determined using the percentage of BrdU+SOX1+ cells, which was calculated as BrdU+SOX1+/DAPI+ cells for non-virus-transduced cells and BrdU+SOX1+GFP+/GFP+ cells for GFP-expressing virus-transduced cells. For differentiation, NSCs were switched to differentiation medium containing N2 and B27 (1:1) with 1 µM retinoic acid and 0.5% FBS in DMEM F12 media. Cells were allowed to differentiate for 2 weeks, followed by immunostaining for Tuj1. The neuronal differentiation rate was determined using the percentage of Tuj1+ cells, which was calculated as Tuj1+/DAPI+ cells for non-virus-transduced cells and Tuj1+GFP+/GFP+ cells for GFP-expressing virus-transduced cells.

Statistical analysis. Student's t-test and ANOVA were used for statistical analyses for comparison of experimental results as reported in each figure and legend. All results were expressed as mean±s.d. The sample size was chosen based on our preliminary studies. Statistical significance was defined as $p<0.05$, $p<0.01$ or $p<0.001$ as specified in the figure legend. No samples, mice or data points were excluded from the reported analyses. No randomization was used for sample assignment and data collection, and no blinding was performed.

EXAMPLE 2

TLX Represses miR-219 Processing

Figure 1:
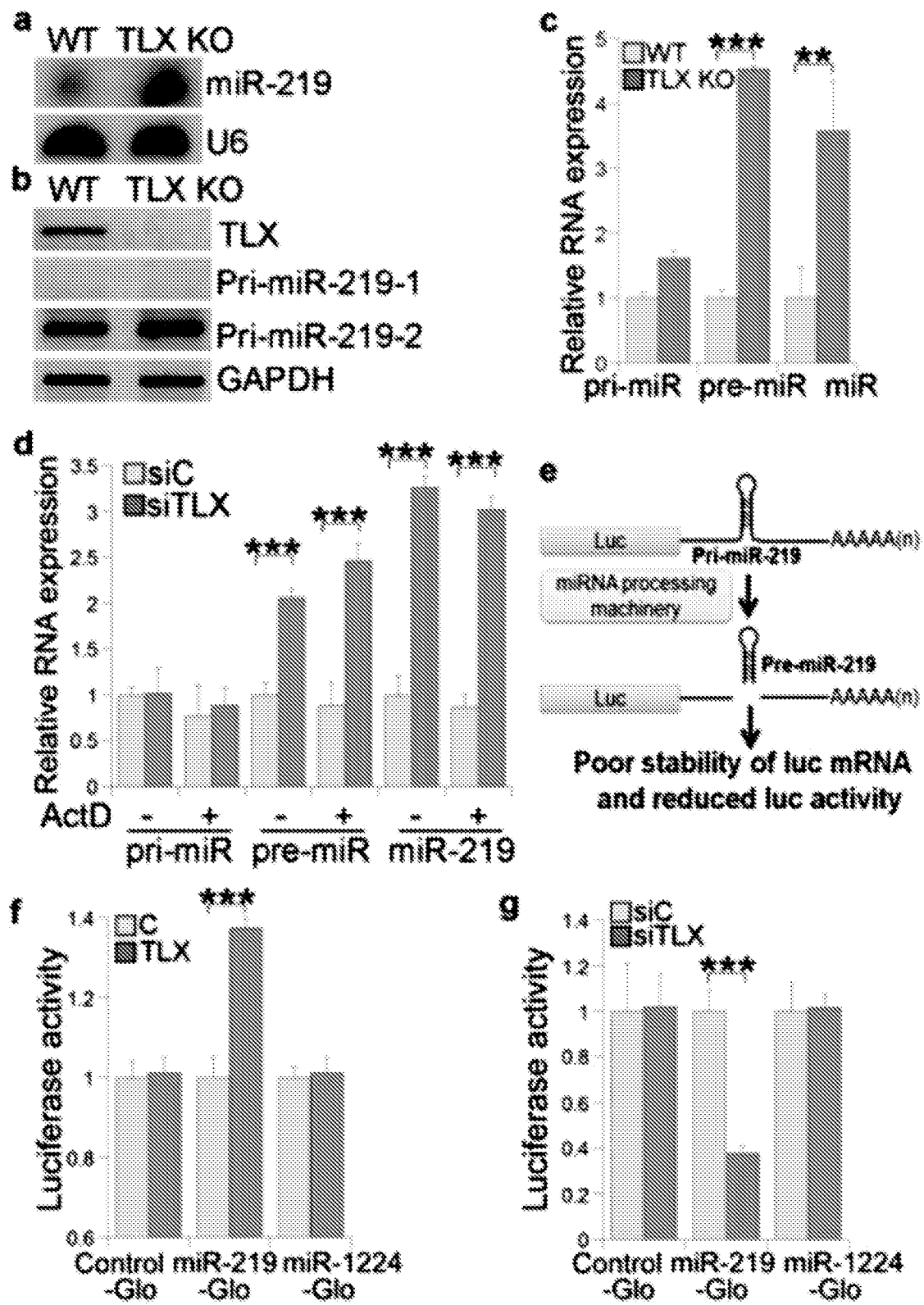
FIGS. 1a-1g illustrate that TLX inhibits miR-219 processing in NSCs.

When comparing gene expression in wild type (WT) and TLX knockout (KO) mouse brains, dramatically elevated expression of miR-219 were detected in TLX KO brains (FIG. 1a). Because TLX is a transcription factor, the level of primary transcripts of miR-219 was examined next. miR-219 is derived from two primary transcripts, pri-miR-219-1 and pri-miR-219-2. No expression of pri-miR-219-1 was detected in both WT and TLX KO brains, and not much change in the expression of pri-miR-219-2 was observed in WT and TLX KO brains either (FIGS. 1b & 1c). Because pri-miR-219-2 was only detected in the brain, pri-miR-219-2 is referred to as pri-miR-219 hereafter.

The expression levels were determined for the precursor form of miR-219 (pre-miR-219) in TLX KO brains. The level of pre-miR-219 increased substantially in TLX KO brains, compared to WT brains, similar to the change in mature miR-219 level, whereas no dramatic change was observed in pri-miR-219 level (FIG. 1c). The levels of all three forms of miR-219 in TLX knockdown NSCs were examined. Knockdown of TLX by siRNA was confirmed by RT-PCR (FIG. 9). Consistent with observation in TLX KO brains, considerable increase in the levels of pre-miR-219 and mature miR-219 was seen in TLX knockdown NSCs, compared to control NSCs, whereas minimal change was detected in the level of pri-miR-219 (FIG. 1d). The up-regulation of pre-miR-219 and mature miR-219 by TLX knockdown was not affected by the treatment of the transcriptional inhibitor actinomycin D (FIG. 1d). These results suggest that TLX regulates the expression level of miR-219 at the post-transcriptional level, presumably through inhibiting the processing of miR-219 from the primary form to the precursor form.

To confirm that TLX plays a role in miR-219 processing, a luciferase-based processing assay was performed. HEK293T cells were transfected with a luciferase reporter construct containing pri-miR-219 sequences that include the Drosha/DGCR8 binding sites. The pri-miR-219 sequences were placed between the coding region of the luciferase gene and its polyadenylation signal. Cleavage of polyadenylation tails from the luciferase transcripts by Drosha/DGCR8 would induce degradation of the luciferase transcripts and reduce luciferase activity (FIG. 1e). It was found that ectopic expression of TLX in HEK293T cells reduced miR-219 processing, as revealed by increased luciferase activity of miR-219-Glo (FIG. 1f). Expression of TLX had no effect on luciferase activity of miR-1224-Glo, a reporter that contains part of miR-1224, an miRtron that is processed into pre-miRNA independent of Drosha cleavage[33] (FIG. 1f). In contrast to overexpression of TLX, knockdown of TLX in NSCs promoted miR-219 processing, as shown by reduced luciferase activity of miR-219-Glo, compared to control RNA-treated cells (FIG. 1g), but had no effect on luciferase activity of miR-1224-Glo (FIG. 1g). These results indicate that TLX negatively regulates miR-219 processing from the primary form to the precursor form.

EXAMPLE 3

TLX Interacts with the miRNA Processing Machinery

Figure 2:
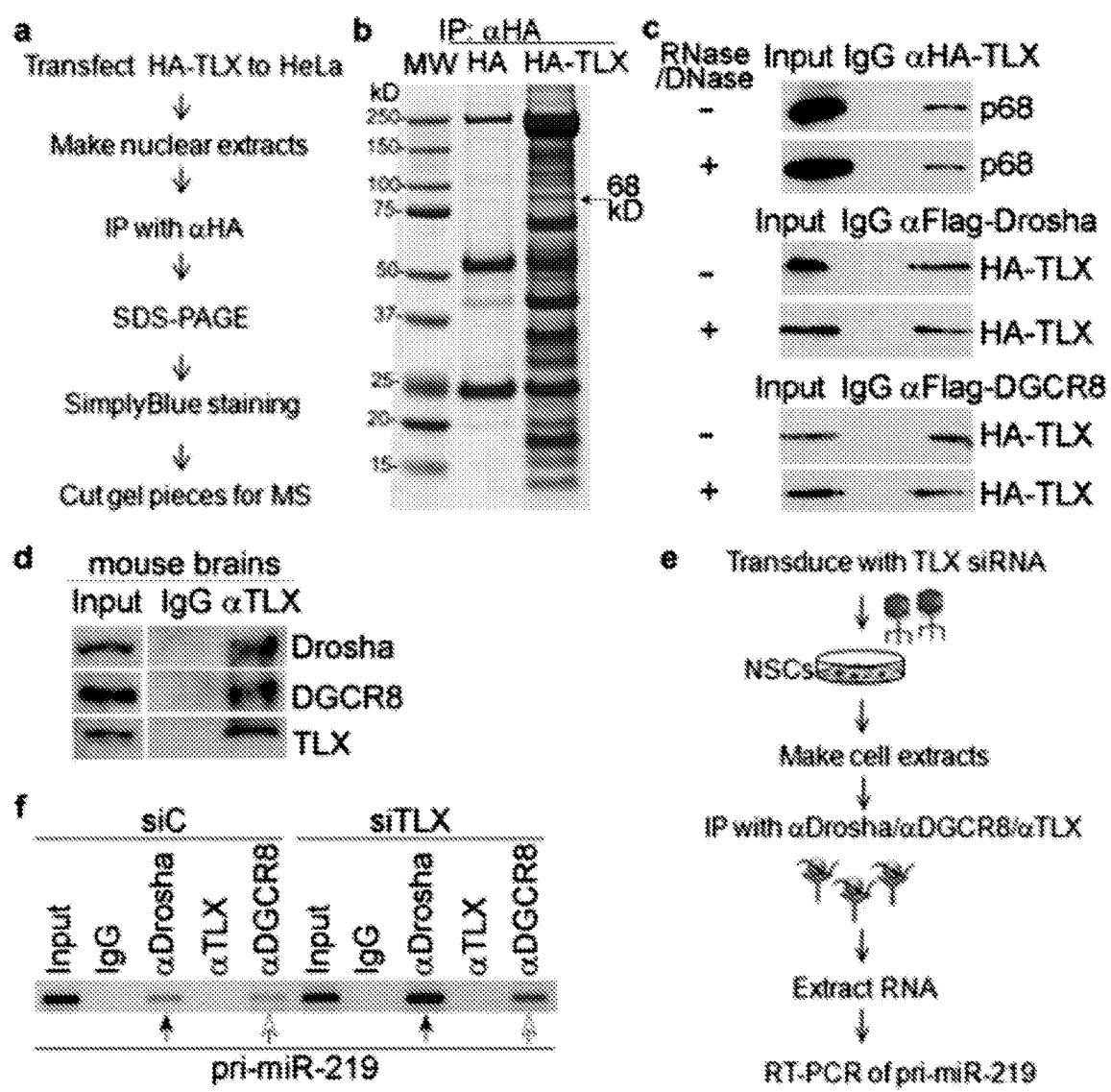
FIGS. 2a-2f illustrate that TLX interacts with the miRNA processing machinery.

In a parallel effort, novel TLX-interacting proteins were identified. Nuclear extracts of HA-TLX-expressing HeLa cells were immunoprecipitated with an HA antibody. Proteins specifically pulled down in HA-TLX-expressing cells, but not in control cells, were subjected to mass spectrometry analysis to determine their identity (FIG. 2a, b). The RNA helicase p68 is among the proteins that were uniquely represented in the pull-downs of HA-TLX-expressing cells. Seventeen peptides of p68 were detected in the HA immunoprecipitates of HA-TLX-expressing cells, but not in that of control HA-expressing cells.

To confirm the interaction of TLX with p68, HEK293T cells were transfected with HA-TLX. p68 was detected in the HA-TLX immunocomplex and the interaction was not affected by the treatment with DNase and RNase (FIG. 2c). Because p68 is a component of the Drosha complex that processes pri-miRNAs into pre-miRNAs [18,19], it was hypothesized that TLX could interact with the miRNA processing machinery via its interaction with p68. To test whether TLX interacts with Drosha and DGCR8, HEK293T cells were transfected with Flag-Drosha or Flag-DGCR8 and HA-TLX. HA-TLX was detected in the immunocomplexes of both Flag-Drosha and Flag-DGCR8, independently of DNase and RNase treatment (FIG. 2c).

To confirm the interaction of endogenous TLX with Drosha/DGCR8, E13.5 mouse brains were harvested, where TLX is highly expressed [4]. Brain lysates were immunoprecipitated with a TLX-specific antibody. Both Drosha and DGCR8 were detected in the TLX immunocomplex (FIG. 2d). These results indicate that TLX interacts with components of the miRNA processing machinery.

The interaction of TLX with Drosha and DGCR8 led us to hypothesize that TLX could inhibit miR-219 processing by preventing the miRNA processing machinery from binding to pri-miR-219. Cell lysates were made from NSCs transduced with lentivirus expressing TLX siRNA and performed RNA immunoprecipitation to determine if knockdown of TLX would affect the binding of Drosha and DGCR8 to pri-miR-219 (FIG. 2e). Weak binding of Drosha and DGCR8 to pri-miR-219 was detected in NSCs transduced with lentivirus expressing a control RNA, and no binding of TLX to pri-miR-219 was detected (FIG. 2f). Knockdown of TLX increased the binding of both Drosha and DGCR8 to pri-miR-219 substantially. These results indicated that TLX inhibits Drosha and DGCR8 from binding to pri-miR-219.

EXAMPLE 4 miR-219 Inhibits Mammalian NSC Proliferation

Figure 3:
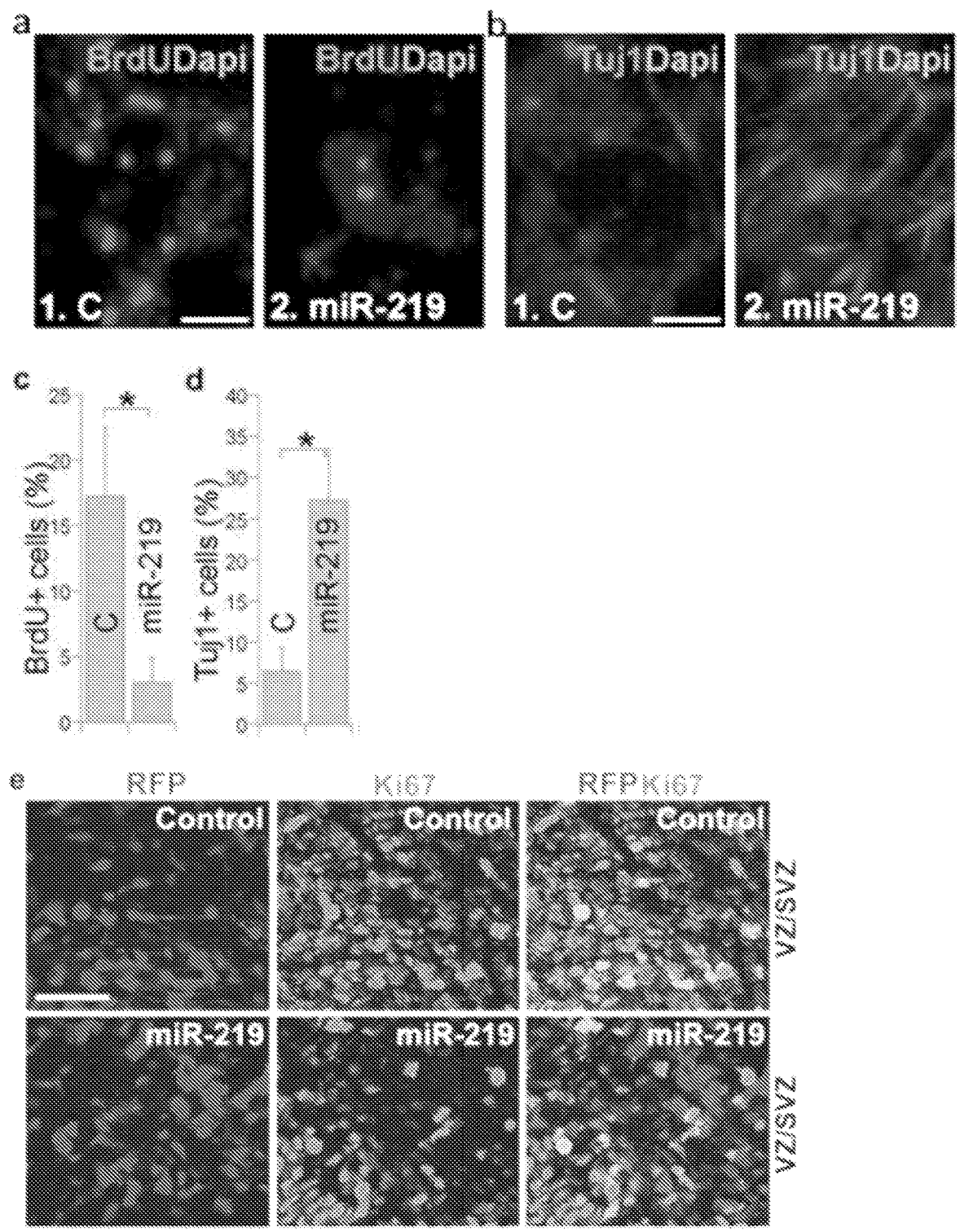
FIGS. 3a-3j illustrate that miR-219 inhibits NSC proliferation & promotes neuronal differentiation.
Figure 3:
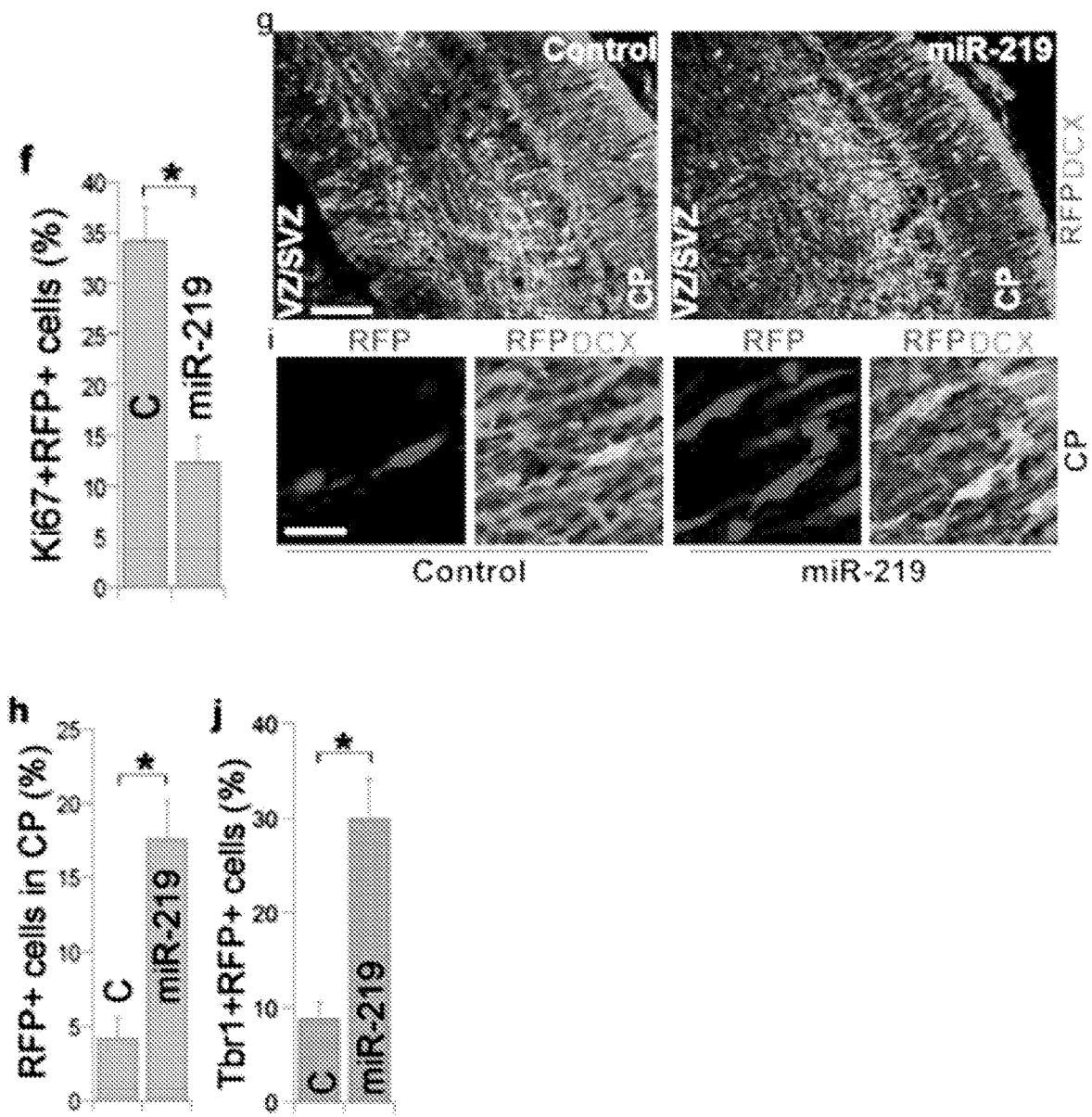

Because TLX plays an important role in regulating mammalian NSC proliferation and differentiation [3,4], the observation that TLX regulates miR-219 processing in mouse NSCs led to a hypothesis that miR-219 could be involved in regulating mammalian NSC phenotypes. To test whether miR-219 affects mammalian NSC proliferation, NSCs were isolated from E14.5 mouse brains and treated with the miR-219 RNA duplex. BrdU labeling was performed to monitor cell proliferation. Treatment with miR-219 reduced cell proliferation substantially (FIG. 3a, c), but had minimal cytotoxicity (FIG. 10a). These results indicate that miR-219 inhibits mammalian NSC proliferation. The effect of miR-219 was then tested on NSC differentiation. E14.5 mouse NSCs were treated with the miR-219 RNA duplex and cultured in differentiation medium. Treatment with miR-219 increased the percentage of βIII tubulin (Tuj1)-positive neurons substantially, compared to treatment with a control RNA (FIG. 3b, d). These results indicate that miR-219 promotes mammalian NSC differentiation into neurons.

To determine the effect of miR-219 on NSC regulation in vivo, miR-219 RNA duplex was electroporated together with an RFP-expressing vector into NSCs of E13.5 embryonic brains in utero. The brains were dissected at E15.5 and analyzed by immunohistochemistry. Immunostaining with Ki67, a proliferation marker, revealed that overexpression of miR-219 decreased cell proliferation in the ventricular zone and subventricular zone (VZ/SVZ) of mouse brains, where NSCs reside (FIG. 3e, f). To determine the effect of miR-219 overexpression on neuronal differentiation, immunostaining with doublecortin (DCX), a neuronal marker, was performed. Compared to control RNA-transfected cells, substantially more miR-219-electroporated (RFP+) cells migrated from VZ/SVZ to the cortical plate (CP), where neurons are located (FIG. 3g, h). Moreover, the RFP+ cells migrated to the CP were positive for DCX (FIG. 3i), confirming their neuronal identity. Immunostaining with Tbr1, another neuronal marker, was also performed. Quantification of the RFP+ cells that expressed Tbr1 revealed a much higher percentage of Tbr1+RFP+ cells in miR-219-electroporated brains than that in control RNA-electroporated brains (FIG. 3j). miR-219 has been shown to induce oligodendrocyte differentiation in in utero electroporated mouse brains harvested at E17.5 [27]. However, the induction of either astrocyte marker GFAP or oligodendrocyte marker MBP expression was not detected in miR-219-electroporated brains harvested at E15.5 (FIGS. 10b and 10c), presumably because brains were analyzed at an early cortical developmental stage when neurogenesis is active but gliogenesis is not yet. These results indicate that miR-219 inhibits mammalian NSC proliferation and promotes their neuronal differentiation during early brain development.

EXAMPLE 5 miR-219 Acts Downstream of TLX to Regulate NSC Phenotypes

Figure 4:
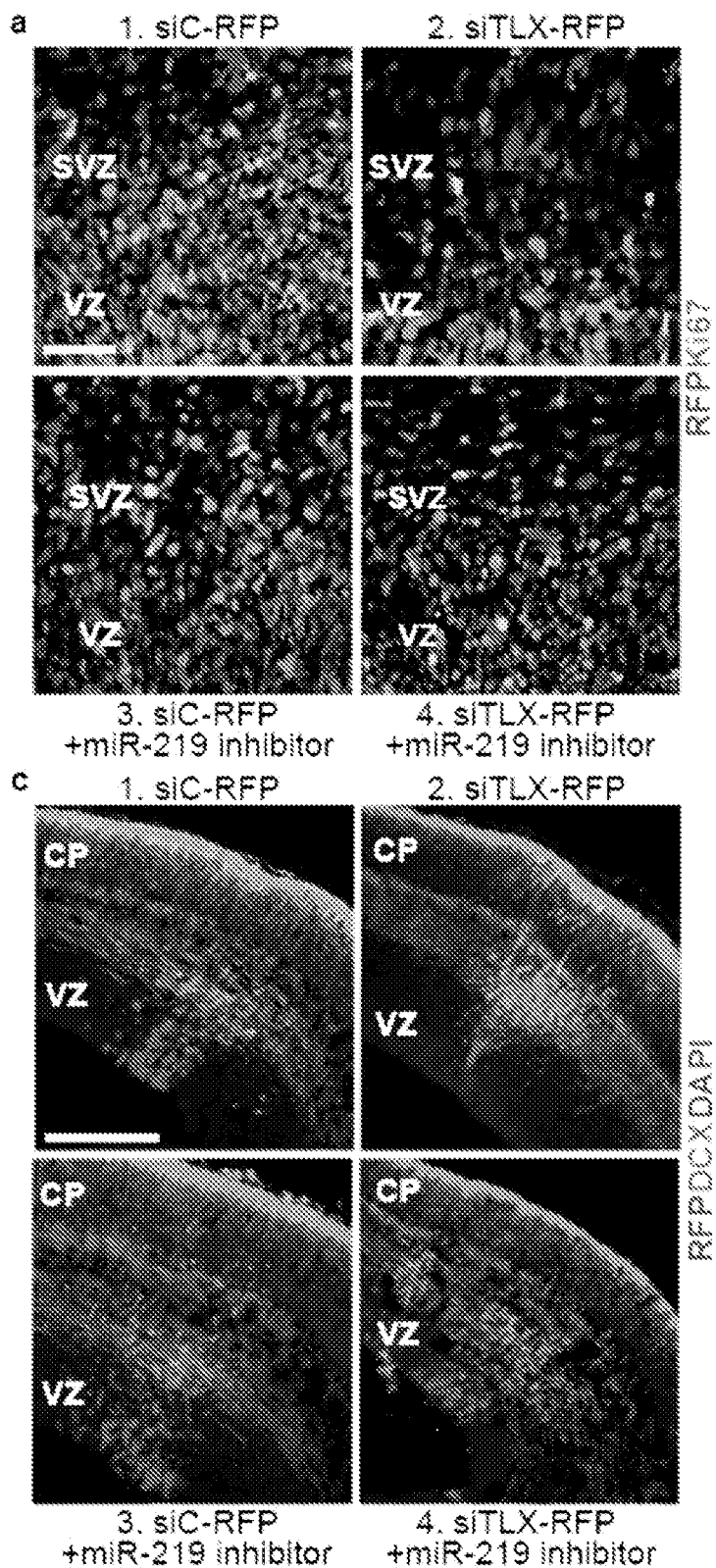
FIGS. 4a-4d illustrate that an miR-219 inhibitor reversed NSC phenotypes induced by TLX siRNA in vivo.

To confirm that miR-219 acts downstream of TLX in NSCs, the effect of TLX knockdown on NSC proliferation and differentiation was tested to see if they could be rescued by an miRNA hairpin inhibitor that is designed specifically to inhibit miR-219 action by interfering with miR-219 binding to downstream targets. When TLX siRNA was electroporated into the VZ/SVZ of E13.5 mouse brains, the percentage of RFP+Ki67+ cells was decreased dramatically, compared to that in control RNA-electroporated brains. However, when TLX siRNA and the miR-219 inhibitor RNA were co-electroporated, the percentage of RFP+Ki67+ cells was recovered substantially (FIG. 4a, b). On the other hand, an increasing number of TLX siRNA-electroporated cells migrated to the CP, compared to control cells (FIG. 4c, d). This phenotype is similar to the effect induced by electroporation of miR-219 into the VZ/SVZ of mouse brains (FIG. 3g, h). In brains co-electroporated with TLX siRNA and the miR-219 inhibitor, the percentage of transfected cells that migrated to the CP was also restored towards the control level (FIG. 4c, d). These results indicate that miR-219 is an important TLX downstream target in regulating mammalian NSC proliferation and differentiation in vivo.

EXAMPLE 6

PDGFRα is a Target Gene of miR-219 and TLX in NSCs

To uncover mechanisms underlying miR-219-mediated regulation of NSC phenotypes, potential miR-219 target genes were identified using TargetScan, which revealed a set of candidate miR-219 targets, the 3' UTR of which can base pair with miR-219. Among the candidate targets, PDGFRα is a confirmed miR-219 target [26] and is expressed in NSCs [34]. RT-PCR showed that the expression of PDGFRα was dramatically decreased in TLX KO brains (FIG. 11a). Moreover, miR-219 repressed the activity of the luciferase reporter with the wild type PDGFRα 3' UTR, but not the reporter that with the mutant 3' UTR, in which the base pairing with miR-219 was destroyed (FIG. 11b), suggesting that miR-219 inhibits PDGFRα expression.

Moreover, the expression of PDGFRα, similar to TLX, was relatively high in NSCs but low in neurons, whereas the expression of miR-219 was relatively low in NSCs but increased in neurons, inversely correlating to the expression of PDGFRα and TLX (FIGS. 11c-e), supporting the concept that TLX represses the expression of miR-219, while miR-219 inhibits the expression of PDGFRα.

Whether overexpressing miR-219 or knockdown of TLX regulates PDGFRα expression was tested next. Repression of PDGFRα expression was detected in miR-219-transfected NSCs and TLX siRNA-transfected NSCs, respectively (FIG. 11f), indicating that PDGFRα indeed acts downstream of miR-219 and TLX. To determine if inhibition of PDGFRα by TLX is mediated through up-regulating miR-219, NSCs were co-transduced with lentivirus expressing TLX siRNA and lentivirus expressing TuD-miR-219, a tough decoy inhibitor [35] of miR-219. Co-expressing TuD-miR-219 with TLX siRNA rescued the inhibition of PDGFRα expression by TLX siRNA substantially (FIG. 11g), suggesting that TLX regulates PDGFRα expression through miR-219. Taken together, these results demonstrate that PDGFRα is a downstream target gene of the TLX-miR-219 regulatory cascade.

How PDGFRα regulates NSC proliferation and differentiation in vivo was studied. In utero electroporation of PDGFRα siRNA into E13.5 mouse brains reduced NSC proliferation as shown by decreased Ki67+RFP+ cells in the VZ/SVZ, whereas the number of RFP+ cells migrated to the CP was increased (FIGS. 12a-d). To determine if PDGFRα is a critical downstream target gene of miR-219 in NSC regulation, if the effect of miR-219 on NSC proliferation and differentiation could be reversed by overexpressing PDGFRα was tested. When PDGFRα and an RFP reporter were electroporated together with miR-219, the number of RFP+Ki67+ cells in the VZ/SVZ increased substantially (FIGS. 13a and 13c), whereas the RFP+ cells that migrated to the CP reduced considerably, compared to that in brains electroporated with RFP and miR-219 only (FIGS. 13b and 13d). These results indicate that PDGFRα is an important downstream target of miR-219 in regulating NSC proliferation and differentiation.

Because the expression of PDGFRα was reduced in TLX knockdown NSCs (FIGS. 11f and 11g), if overexpression of PDGFRα could rescue TLX siRNA-induced inhibition of NSC proliferation was determined. Co-electroporation of PDGFRα with TLX siRNA to E13.5 mouse brains showed an increase in the number of Ki67+RFP+ cells in the VZ/SVZ and a decrease in the number of RFP+ cells migrated to the CP, compared to electroporation with TLX siRNA alone (FIGS. 14a-14d). These results indicate that PDGFRα acts downstream of TLX to regulate NSC proliferation and differentiation in mammalian brains.

EXAMPLE 7

A TLX Peptide Promotes miR-219 Processing

Figure 5:
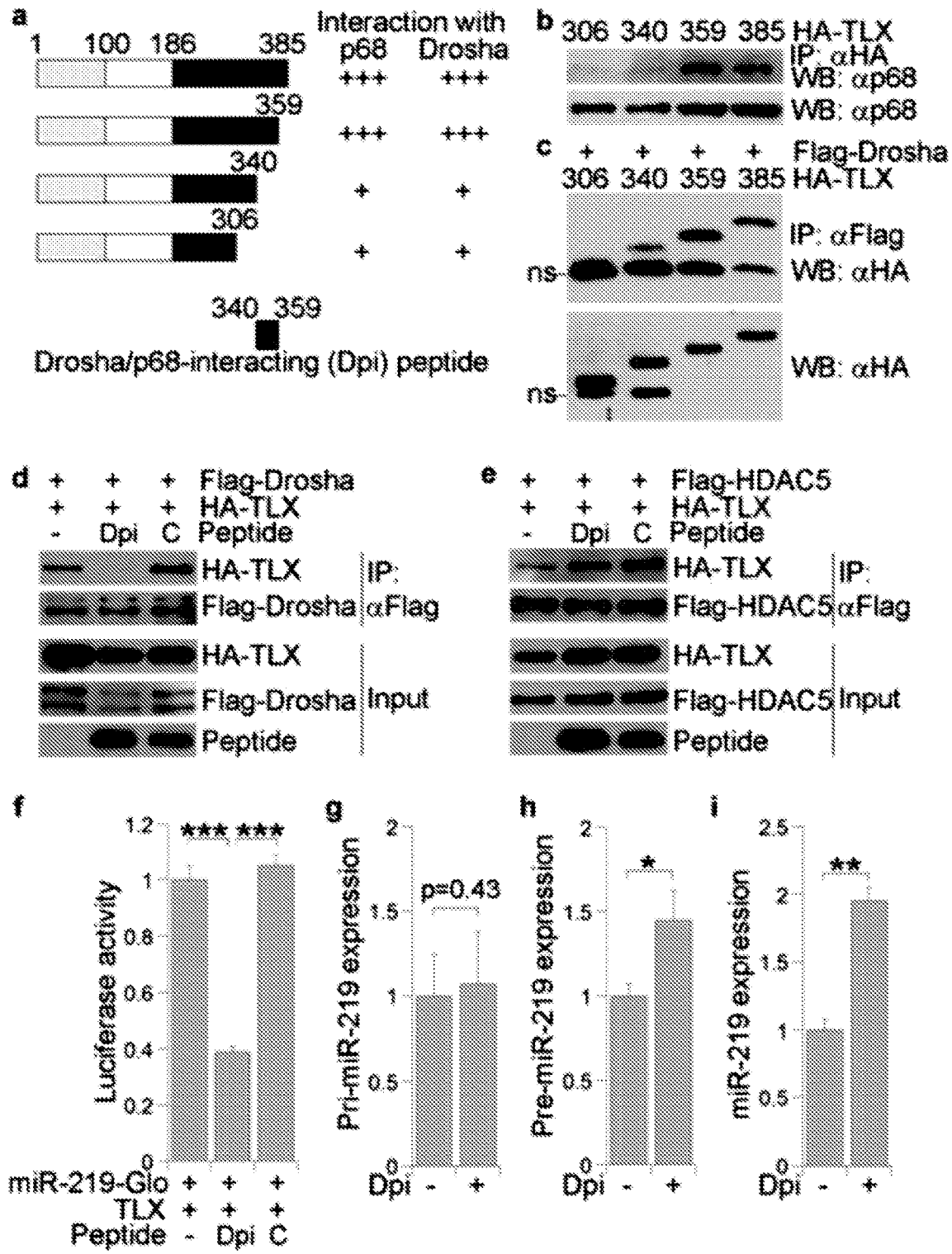
FIGS. 5a-5i illustrate that a TLX peptide promotes miR-219 processing.

To determine the region in TLX that is critical for the interaction with the miRNA processing machinery, the minimal domain of TLX was mapped for p68 and Drosha interactions by serial deletion (FIG. 5a). Co-immunoprecipitation analysis revealed that the TLX residues 340-359 were critical for the TLX-p68 interaction (FIG. 5a, b). Deletion of TLX residues 340-359 also reduced the interaction of TLX with Drosha dramatically (FIG. 5a, c). The TLX region spanning residues 340 to 359 was determined to be the Drosha/p68-interaction (Dpi) domain (FIG. 5a).

To determine whether the Dpi domain interferes with the TLX-Drosha interaction, an HA-tagged TLX peptide containing the Dpi domain (Dpi) was co-expressed with HA-tagged full-length TLX (HA-TLX) and Flag-Drosha in HEK293T cells. The interaction of TLX with Drosha, as determined by co-immunoprecipitation, was substantially reduced when Dpi was co-expressed, compared to that when an empty vector (–) or a control peptide (C) was expressed (FIG. 5d). To determine the specificity of Dpi on the interaction of TLX with its interacting partners, Dpi was expressed together with HA-TLX and Flag-HDAC5, a known transcriptional corepressor of TLX [11]. In contrast to the interaction of TLX with Drosha, the interaction of TLX with HDAC5 was not blocked by Dpi (FIG. 5e). These results indicate that Dpi specifically interferes with the interaction of TLX with Drosha, but not the interaction of TLX with a transcriptional coregulator.

To determine if the interaction between TLX and the miRNA processing machinery is critical for regulation of miR-219 processing by TLX, Dpi was used to block the interaction of TLX with the miRNA processing machinery and miR-219-Glo, a luciferase reporter containing the pri-miR-219 sequence in its 3' UTR to monitor miR-219 processing. Co-transfection of TLX with Dpi reduced the luciferase activity substantially, compared to transfection with TLX alone (FIG. 5f), suggesting that expression of Dpi promoted miR-219 processing from pri-miR-219. In contrast, a control peptide that contains TLX residues outside the Dpi domain failed to boost miR-219 processing (FIG. 5f).

The Dpi peptide was electroporated into NSCs and determined miR-219 processing by evaluating the levels of the three forms of miR-219, pri-miR-219, pre-miR-219 and mature miR-219. The levels of both pre-miR-219 and mature miR-219 forms increased considerably, whereas no significant change was detected in the level of pri-miR-219 (FIGS. 5g-5i). These results further demonstrate that expressing the Dpi peptide promotes miR-219 processing but has no effect on the transcription of pri-miR-219.

Figure 6:
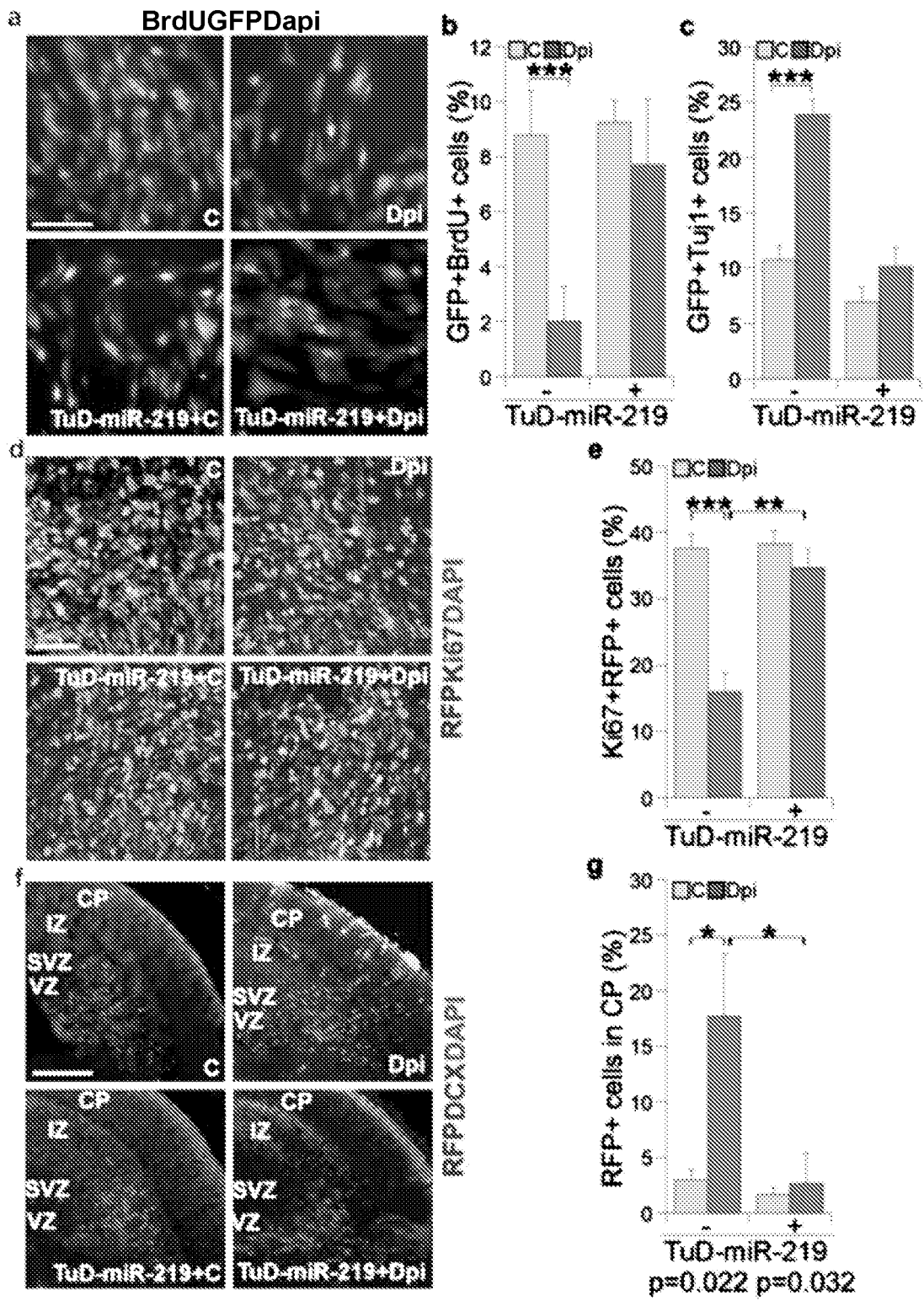
FIGS. 6a-6g illustrate that the Dpi peptide regulates NSC proliferation and differentiation.

Whether expressing Dpi could affect NSC proliferation and differentiation was tested. NSCs from E14.5 mouse brains were transduced with lentivirus expressing Dpi or a control peptide and a GFP reporter. Compared to the control peptide, expression of Dpi reduced cell proliferation substantially (FIGS. 6a and 6b). To determine if inhibition of NSC proliferation by Dpi is mediated by modulating miR-219, NSCs were co-transduced with Dpi and the miR-219 decoy inhibitor, TuD-miR-219. Expressing TuD-miR-219 rescued the Dpi-mediated inhibition of NSC proliferation substantially (FIGS. 6a and 6b), suggesting that Dpi regulates NSC proliferation through modulating miR-219. Treatment with Dpi also increased the percentage of Tuj1-positive neurons significantly, compared to treatment with the control peptide, and co-expressing TuD-miR-219 reversed this effect largely (FIG. 6c). These results together indicate that the Dpi peptide inhibits NSC proliferation and promotes neuronal differentiation by modulating miR-219 expression.

To determine the effect of Dpi on NSC proliferation and differentiation in vivo, a vector expressing a control peptide or Dpi was electroporated together with an RFP reporter into E13.5 mouse brains in uterus. Expression of Dpi decreased Ki67+RFP+ cells in the VZ/SVZ, compared to expression of the control peptide. Co-electroporating Dpi with TuD-miR-219 rescued the reduced cell proliferation induced by Dpi (FIGS. 6d and 6e). These results indicate that Dpi inhibits NSC proliferation in vivo, presumably through regulating miR-219 expression. On the other hand, more RFP+ cells that had been electroporated with the Dpi-expressing vector migrated from the VZ/SVZ to the CP. Co-electroporating Dpi with TuD-miR-219 reversed the precocious migration largely (FIGS. 6f and 6g). These results indicate that Dpi promotes neuronal differentiation in vivo through modulating miR-219 action. Together with the observation that Dpi promotes miR-219 processing (FIGS. 5f-5i), these results suggest that modulation of miR-219 processing by TLX regulates NSC proliferation and differentiation.

EXAMPLE 8

Elevated miR-219 Expression Inhibits SCZ NSC Proliferation

Elevated expression of miR-219 has been observed in various brain regions of SCZ patients [29,30,32]. Whether miR-219 expression is altered in SCZ NSCs was tested by obtaining induced pluripotent stem cells (iPSCs) derived from SCZ patients (D1 & D2, FIG. 7a) of pedigree H [36] with a 4 bp deletion in the coding sequence of the DISC1 gene [37,38]. This deletion causes a frameshift and premature termination of translation in DISC1 [37,38]. The SCZ iPSCs were differentiated into NSCs. Wild type (WT) NSCs derived from iPSCs of unaffected individuals (C1, C2 and C3) were used as controls [37,38]. Both SCZ and WT iPSC-derived NSCs expressed human NSC markers SOX1 and NESTIN (FIG. 7b).

RT-PCR revealed that the level of miR-219 increased substantially in DISC1-mutant SCZ NSCs, compared to WT control NSCs (FIG. 7c). To determine if the DISC1 mutation is sufficient to induce elevated miR-219 expression in NSCs, the isogenic iPSC lines C1 M and C3M were used, in which the 4 bp deletion seen in the SCZ patients was introduced into the DISC1 gene in the WT control iPSC lines C1 and C3 [38]. Similar to what was seen in the SCZ NSCs, a considerable increase was observed in miR-219 level in C1M and C3M NSCs, compared to that in their isogenic WT controls (FIG. 7c). These results together indicate that miR-219 expression is elevated in NSCs of DISC1-mutant SCZ patients and that a DISC1 mutation is sufficient to induce miR-219 up-regulation in NSCs. In contrast to elevated miR-219 expression, reduced expression of TLX was observed in both the DISC1-mutant SCZ NSCs (D1 & D2) and the genetically engineered C1 M and C3M NSCs that contain the DISC1 mutation (FIG. 7d). The inverse correlation between TLX and miR-219 expression in SCZ NSCs further supports the hypothesis that TLX negatively regulates miR-219 level in NSCs.

Reduced NSC proliferation has been observed in postmortem brain specimens from SCZ patients [39] and DISC1 has been shown to regulate NSC proliferation in the developing mouse cortex [40,41]. However, whether DISC1 regulates cell proliferation in human NSCs and whether mutant DISC1 induces abnormal NSC proliferation remained unknown. The results showing that mutant DISC1 induces elevated expression of miR-219 in SCZ NSCs led to a hypothesis that increased expression of miR-219 induced by mutant DISC1 could result in abnormal cell proliferation in SCZ NSCs. To test this hypothesis, cell proliferation in WT and DISC1-mutant SCZ NSCs was compared by BrdU and SOX1 double labeling. The percentage of BrdU+ SOX1+ cells was significantly reduced in DISC1-mutant SCZ NSCs, compared to that in WT control NSCs (FIG. 7e). To test whether the DISC1 mutation is sufficient for the observed proliferative defects, cell proliferation in NSCs derived from the isogenic iPSC lines C1, C1M, and C3, C3M was compared. The decrease in NSC proliferation observed in SCZ NSCs was recapitulated in C1M and C3M NSCs (FIG. 7e). To determine if abnormal expression of miR-219 in D/SCI-mutant NSCs tips the balance between human NSC proliferation and differentiation, neuronal differentiation in WT and DISC1-mutant NSCs under a spontaneous differentiation condition was compared. Quantification of Tuj1+ neuronal cells revealed increased neuronal differentiation in DISC1-mutant NSCs, compared to WT NSCs (FIG. 7f), consistent with the observation of reduced NSC proliferation in DISC1-mutant NSCs (FIG. 7e).

To determine if elevated miR-219 expression is sufficient to reduce cell proliferation in human NSCs, miR-219 was overexpressed in WT NSCs using an miR-219-expressing retroviral vector and NSC proliferation was determined by BrdU and SOX1 double labeling. Reduced cell proliferation was observed in miR-219-overexpressing WT NSCs compared to control vector-expressing WT NSCs, in a manner similar to the reduced cell proliferation observed in DISC1-mutant NSCs when compared to WT NSCs (FIG. 8a). In parallel, the miR-219-overexpressing WT NSCs were induced for neuronal differentiation. The rate of neuronal differentiation was determined by the percentage of Tuj1+ cells. Overexpression of miR-219 in WT NSCs also increased neuronal differentiation rate, compared to that in control vector-treated WT NSCs (FIG. 15a). These results indicate that elevated miR-219 expression is sufficient to inhibit cell proliferation in human NSCs. Together with the observation that miR-219 expression is abnormally up-regulated in SCZ NSCs, these results suggest that the abnormally elevated miR-219 expression could be an underlying factor for reduced NSC proliferation observed in SCZ patients.

To determine if the proliferative defect in DISC1-mutant NSCs indeed resulted from abnormally elevated miR-219 expression, miR-219 in D/SCI-mutant NSCs was inhibited using TuD-miR-219. NSC proliferation was monitored by BrdU and SOX1 double labeling. Treating the DISC1-mutant NSCs (D1, D2, C1M and C3M) with TuD-miR-219 increased the proliferative rate in these cells substantially, largely rescuing the proliferative defects of the DISC1-mutant NSCs (FIG. 8b). Treatment with TuD-miR-219 also reversed the elevated differentiation in DISC1-mutant NSCs considerably, as revealed by the reduced percentage of Tuj1+ cells, compared to that in cells treated with a control vector (FIG. 15b). These results indicate that miR-219 plays an important role in regulating cell proliferation in DISC1-mutant SCZ NSCs and that an miR-219 inhibitor could rescue the proliferative defect in these cells.

Figure 7:
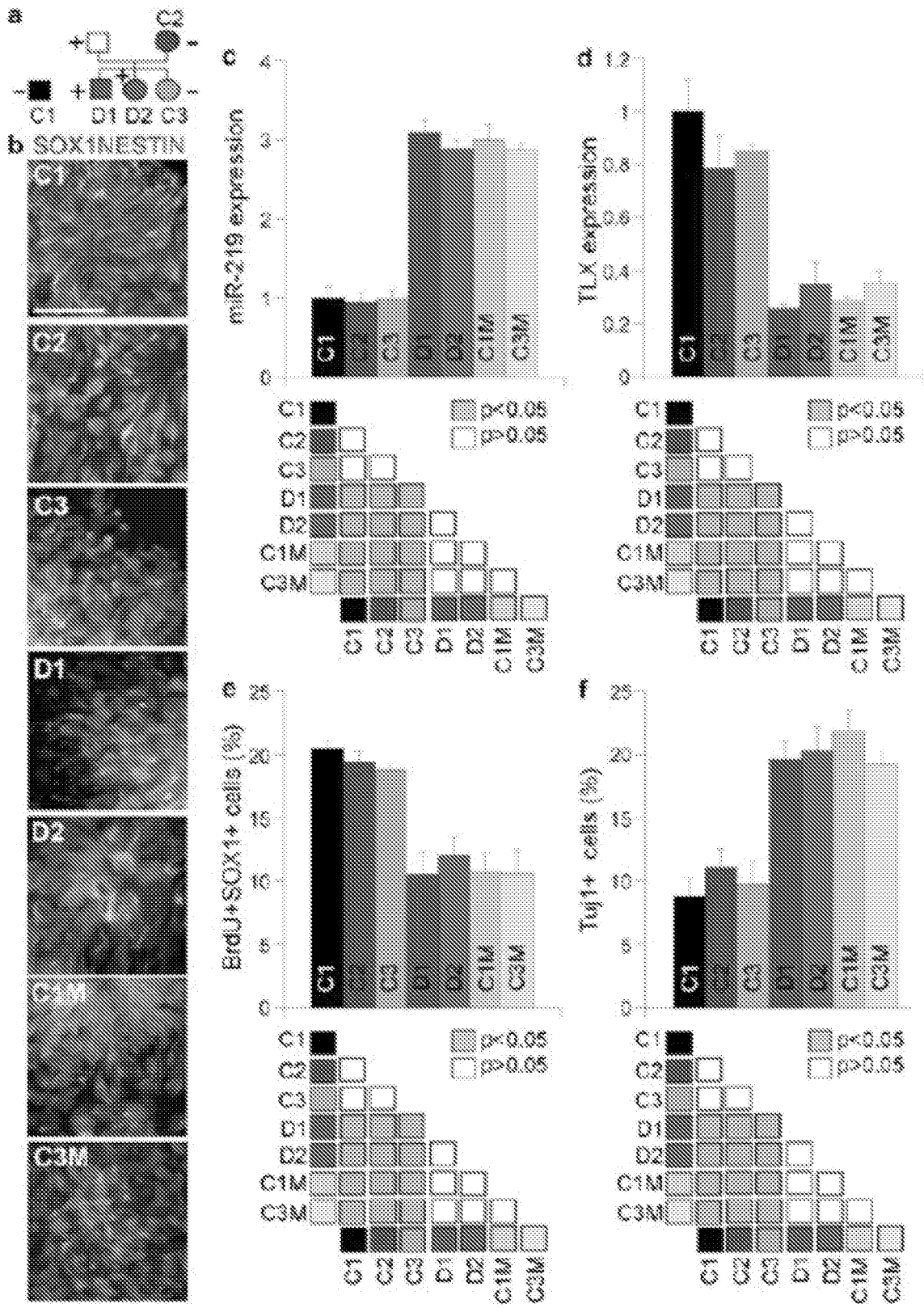

In addition to elevated miR-219 expression in D/SCI-mutant SCZ NSCs, reduced expression of TLX in D/SCI-mutant SCZ NSCs was also detected (FIG. 7). To test if TLX knockdown is able to reduce cell proliferation in human NSCs, WT NSCs were transduced with a TLX siRNA-expressing lentiviral vector. Reduced cell proliferation was observed in TLX knockdown WT NSCs, compared to control vector-transduced WT NSCs (FIG. 8c). To test if increase of TLX expression could rescue the proliferative defect in SCZ NSCs, TLX in DISC1-mutant NSCs was overexpressed. Elevated expression of TLX in DISC1-mutant NSCs increased cell proliferation (FIG. 8d), consistent with the observation in DISC1-mutant NSCs treated with TuD-miR-219 (FIG. 8b). These results together indicate that the TLX-miR-219 cascade is important in regulating cell proliferation in DISC1-mutant SCZ NSCs.

All publications and patent documents cited herein are incorporated by reference.

REFERENCES

1 Yu, R. T., McKeown, M., Evans, R. M., and Umesono, K. Relationship between Drosophila gap gene tailless and a vertebrate nuclear receptor Tlx. *Nature* 370, 375-379 (1994).

2 Monaghan, A. P., Bock, D., Gass, P., Schwager, A., Wolfer, D. P., Lipp, H. P., and Schutz, G. Defective limbic system in mice lacking the tailless gene. *Nature* 390, 515-517 (1997).

3 Shi, Y., Lie, C. D., Taupin, P., Nakashima, K., Ray, J., Yu, R. T., Gage, F. H., and Evans, R. M. Expression and function of orphan nuclear receptor TLX in adult neural stem cells. *Nature* 427, 78-83 (2004).

4 Li, W., Sun, G., Yang, S., Qu, Q., Nakashima, K., and Shi, Y. Nuclear Receptor TLX Regulates Cell Cycle Progression in Neural Stem Cells of the Developing Brain. *Mol Endocrinol* 22, 56-64 (2008).

5 Qu, Q., Sun, G., Li, W., Yang, S., Ye, P., Zhao, C., Yu, R. T., Gage, F. H., Evans, R. M., and Shi, Y. Orphan nuclear receptor TLX activates Wnt/beta-catenin signalling to stimulate neural stem cell proliferation and self-renewal. *Nat Cell Biol* 12, 31-40; sup pp 31-39 (2010).

6 Zhang, C. L., Zou, Y., He, W., Gage, F. H., and Evans, R. M. A role for adult TLX-positive neural stem cells in learning and behaviour. *Nature* 451, 1004-1007 (2008).

7 Murai, K., Qu, Q., Sun, G., Ye, P., Li, W., Asuelime, G., Sun, E., Tsai, G. E., and Shi, Y. Nuclear receptor TLX stimulates hippocampal neurogenesis and enhances learning and memory in a transgenic mouse model. *Proc Natl Acad Sci USA* 111, 9115-9120 (2014).

8 Roy, K., Kuznicki, K., Wu, Q., Sun, Z., Bock, D., Schutz, G., Vranich, N., and Monaghan, A. P. The Tlx gene regulates the timing of neurogenesis in the cortex. *J Neurosci* 24, 8333-8345 (2004).

9 Stenman, J. M., Wang, B., and Campbell, K. Tlx controls proliferation and patterning of lateral telencephalic progenitor domains. *J Neurosci* 23, 10568-10576 (2003).

10 Zhao, C., Sun, G., Li, S., Lang, M., Yang, S., Li, W., and Shi, Y. microRNA let-7b regulates neural stem cell proliferation and differentiation by targeting nuclear receptor TLX signaling. *Proc Natl Acad Sci USA* 107, 1876-1881 (2010).

11 Sun, G., Yu, R. T., Evans, R. M., and Shi, Y. Orphan nuclear receptor TLX recruits histone deacetylases to repress transcription and regulate neural stem cell proliferation. *Proc Natl Acad Sci USA* 104, 15282-15287 (2007).

12 Sun, G., Alzayady, K., Stewart, R., Ye, P., Yang, S., Li, W., and Shi, Y. Histone demethylase LSD1 regulates neural stem cell proliferation. *Mol Cell Biol* 30, 1997-2005 (2010).

13 Yokoyama, A., Takezawa, S., Schule, R., Kitagawa, H., and Kato, S. Transrepressive function of TLX requires the histone demethylase LSD1. *Mol Cell Biol* 28, 3995-4003 (2008).

14 Zhao, C., Sun, G., Li, S., and Shi, Y. A feedback regulatory loop involving microRNA-9 and nuclear receptor TLX in neural stem cell fate determination. *Nature Struct Mol Biol* 16, 365-371 (2009).

15 Iwahara, N., Hisahara, S., Hayashi, T., and Horio, Y. Transcriptional activation of NAD+-dependent protein deacetylase SIRT1 by nuclear receptor TLX. *Biochem Biophys Res Commun* 386, 671-675 (2009).

16 Elmi, M., Matsumoto, Y., Zeng, Z. J., Lakshminarasimhan, P., Yang, W., Uemura, A., Nishikawa, S., Moshiri, A., Tajima, N., Agren, H., and Funa, K. TLX activates MASH1 for induction of neuronal lineage commitment of adult hippocampal neuroprogenitors. *Mol Cell Neurosci* 45, 121-131 (2010).

17 Bartel, D. P. MicroRNAs: genomics, biogenesis, mechanism, and function. *Cell* 116, 281-297 (2004).

18 Fukuda, T., Yamagata, K., Fujiyama, S., Matsumoto, T., Koshida, I., Yoshimura, K., Mihara, M., Naitou, M., Endoh, H., Nakamura, T., Akimoto, C., Yamamoto, Y., Katagiri, T., Foulds, C., Takezawa, S., Kitagawa, H., Takeyama, K., O'Malley, B. W., and Kato, S. DEAD-box RNA helicase subunits of the Drosha complex are required for processing of rRNA and a subset of microRNAs. Nat Cell Biol 9, 604-611 (2007).

19 Gregory, R. I., Yan, K. P., Amuthan, G., Chendrimada, T., Doratotaj, B., Cooch, N., and Shiekhattar, R. The Microprocessor complex mediates the genesis of microRNAs. Nature 432, 235-240 (2004).

20 Fuller-Pace, F. V. and Ali, S. The DEAD box RNA helicases p68 (Ddx5) and p72 (Ddx17): novel transcriptional co-regulators. Biochem Soc Trans 36, 609-612 (2008).

21 Davis, B. N., Hilyard, A. C., Lagna, G., and Hata, A. SMAD proteins control DROSHA-mediated microRNA maturation. Nature 454, 56-61 (2008).

22 Suzuki, H. I., Yamagata, K., Sugimoto, K., Iwamoto, T., Kato, S., and Miyazono, K. Modulation of microRNA processing by p53. Nature 460, 529-533 (2009).

23 Kawai, S. and Amano, A. BRCA1 regulates microRNA biogenesis via the DROSHA microprocessor complex. J Cell Bio! 197, 201-208 (2012).

24 Cheng, H. Y., Papp, J. W., Varlamova, O., Dziema, H., Russell, B., Curfman, J. P., Nakazawa, T., Shimizu, K., Okamura, H., Impey, S., and Obrietan, K. microRNA modulation of circadian-clock period and entrainment. Neuron 54, 813-829 (2007).

25 Lukiw, W. J. Micro-RNA speciation in fetal, adult and Alzheimer's disease hippocampus. Neuroreport 18, 297-300 (2007).

26 Dugas, J. C., Cuellar, T. L., Scholze, A., Ason, B., Ibrahim, A., Emery, B., Zamanian, J. L., Foo, L. C., McManus, M. T., and Barres, B. A. Dicerl and miR-219 Are required for normal oligodendrocyte differentiation and myelination. Neuron 65, 597-611 (2010).

27 Zhao, X., He, X., Han, X., Yu, Y., Ye, F., Chen, Y., Hoang, T., Xu, X., Mi, Q. S., Xin, M., Wang, F., Appel, B., and Lu, Q. R. MicroRNA-mediated control of oligodendrocyte differentiation. Neuron 65, 612-626 (2010).

28 Hudish, L. I., Blasky, A. J., and Appel, B. miR-219 regulates neural precursor differentiation by direct inhibition of apical par polarity proteins. Dev Cell 27, 387-398 (2013).

29 Beveridge, N. J., Gardiner, E., Carroll, A. P., Tooney, P. A., and Cairns, M. J. Schizophrenia is associated with an increase in cortical microRNA biogenesis. Mol Psychiatry 15, 1176-1189 (2010).

30 Beveridge, N. J., Tooney, P. A., Carroll, A. P., Gardiner, E., Bowden, N., Scott, R. J., Tran, N., Dedova, I., and Cairns, M. J. Dysregulation of miRNA 181b in the temporal cortex in schizophrenia. Hum Mol Genet 17, 1156-1168 (2008).

31 Santarelli, D. M., Beveridge, N. J., Tooney, P. A., and Cairns, M. J. Upregulation of dicer and microRNA expression in the dorsolateral prefrontal cortex Brodmann area 46 in schizophrenia. Biol Psychiatry 69, 180-187 (2011).

32 Smalheiser, N. R., Lugli, G., Zhang, H., Rizavi, H., Cook, E. H., and Dwivedi, Y. Expression of microRNAs and other small RNAs in prefrontal cortex in schizophrenia, bipolar disorder and depressed subjects. PLoS One 9, e86469 (2014).

33 Berezikov, E., Chung, W. J., Willis, J., Cuppen, E., and Lai, E. C. Mammalian mirtron genes. Mol. Cell 28, 328-336 (2007).

34 Jackson, E. L., Garcia-Verdugo, J. M., Gil-Perotin, S., Roy, M., Quinones-Hinojosa, A., VandenBerg, S., and Alvarez-Buylla, A. PDGFR alpha-positive B cells are neural stem cells in the adult SVZ that form glioma-like growths in response to increased PDGF signaling. Neuron 51, 187-199 (2006).

35 Haraguchi, T., Ozaki, Y., and Iba, H. Vectors expressing efficient RNA decoys achieve the long-term suppression of specific microRNA activity in mammalian cells. Nucleic Acids Res 37, e43 (2009).

36 Sachs, N. A., Sawa, A., Holmes, S. E., Ross, C. A., DeLisi, L. E., and Margolis, R. L. A frameshift mutation in Disrupted in Schizophrenia 1 in an American family with schizophrenia and schizoaffective disorder. Mol Psychiatry 10, 758-764 (2005).

37 Chiang, C. H., Su, Y., Wen, Z., Yoritomo, N., Ross, C. A., Margolis, R. L., Song, H., and Ming, G. L. Integration-free induced pluripotent stem cells derived from schizophrenia patients with a DISC1 mutation. Mol Psychiatry 16, 358-360 (2011).

38 Wen, Z., Nguyen, H. N., Guo, Z., Lalli, M. A., Wang, X., Su, Y., Kim, N. S., Yoon, K. J., Shin, J., Zhang, C., Makri, G., Nauen, D., Yu, H., Guzman, E., Chiang, C. H., Yoritomo, N., Kaibuchi, K., Zou, J., Christian, K. M., Cheng, L., Ross, C. A., Margolis, R. L., Chen, G., Kosik, K. S., Song, H., and Ming, G. L. Synaptic dysregulation in a human iPS cell model of mental disorders. Nature (2014).

39 Reif, A., Fritzen, S., Finger, M., Strobel, A., Lauer, M., Schmitt, A., and Lesch, K. P. Neural stem cell proliferation is decreased in schizophrenia, but not in depression. Mol Psychiatry 11, 514-522 (2006).

40 Mao, Y., Ge, X., Frank, C. L., Madison, J. M., Koehler, A. N., Doud, M. K., Tassa, C., Berry, E. M., Soda, T., Singh, K. K., Biechele, T., Petryshen, T. L., Moon, R. T., Haggarty, S. J., and Tsai, L. H. Disrupted in schizophrenia 1 regulates neuronal progenitor proliferation via modulation of GSK3beta/beta-catenin signaling. Cell 136, 1017-1031 (2009).

41 Ishizuka, K., Kamiya, A., Oh, E. C., Kanki, H., Seshadri, S., Robinson, J. F., Murdoch, H., Dunlop, A. J., Kubo, K., Furukori, K., Huang, B., Zeledon, M., Hayashi-Takagi, A., Okano, H., Nakajima, K., Houslay, M. D., Katsanis, N., and Sawa, A. DISC1-dependent switch from progenitor proliferation to migration in the developing cortex. Nature 473, 92-96 (2011).

42 Sarachana, T., Zhou, R., Chen, G., Manji, H. K., and Hu, V. W. Investigation of post-transcriptional gene regulatory networks associated with autism spectrum disorders by microRNA expression profiling of lymphoblastoid cell lines. Genome Med 2, 23 (2010).

43 Saus, E., Soria, V., Escaramis, G., Vivarelli, F., Crespo, J. M., Kagerbauer, B., Menchon, J. M., Urretavizcaya, M., Gratacos, M., and Estivill, X. Genetic variants and abnormal processing of pre-miR-182, a circadian clock modulator, in major depression patients with late insomnia. Hum Mol Genet 19, 4017-4025 (2010).

44 Rivers, L. E., Young, K. M., Rizzi, M., Jamen, F., Psachoulia, K., Wade, A., Kessaris, N., and Richardson, W. D. PDGFRA/NG2 glia generate myelinating oligodendrocytes and piriform projection neurons in adult mice. Nat Neurosci 11, 1392-1401 (2008).

45 Goldberg, J. F. and Chengappa, K. N. Identifying and treating cognitive impairment in bipolar disorder. *Bipolar Disord* 11 Suppl 2, 123-137 (2009).

46 Swayze, V. W., 2nd, Andreasen, N. C., Alliger, R. J., Ehrhardt, J. C., and Yuh, W. T. Structural brain abnormalities in bipolar affective disorder. Ventricular enlargement and focal signal hyperintensities. *Arch Gen Psychiatry* 47, 1054-1059 (1990).

47 Young, K. A., Berry, M. L., Mahaffey, C. L., Saionz, J. R., Hawes, N. L., Chang, B., Zheng, Q. Y., Smith, R. S., Bronson, R. T., Nelson, R. J., and Simpson, E. M. Fierce: a new mouse deletion of Nr2e1; violent behaviour and ocular abnormalities are background-dependent. *Behav Brain Res* 132, 145-158 (2002).

48 Clapcote, S. J., Lipina, T. V., Millar, J. K., Mackie, S., Christie, S., Ogawa, F., Lerch, J. P., Trimble, K., Uchiyama, M., Sakuraba, Y., Kaneda, H., Shiroishi, T., Houslay, M. D., Henkelman, R. M., Sled, J. G., Gondo, Y., Porteous, D. J., and Roder, J. C. Behavioral phenotypes of Disc1 missense mutations in mice. *Neuron* 54, 387-402 (2007).

49 Hikida, T., Jaaro-Peled, H., Seshadri, S., Oishi, K., Hookway, C., Kong, S., Wu, D., Xue, R., Andrade, M., Tankou, S., Mori, S., Gallagher, M., Ishizuka, K., Pletnikov, M., Kida, S., and Sawa, A. Dominant-negative DISC1 transgenic mice display schizophrenia-associated phenotypes detected by measures translatable to humans. *Proc Natl Acad Sci USA* 104, 14501-14506 (2007).

50 Koike, H., Arguello, P. A., Kvajo, M., Karayiorgou, M., and Gogos, J. A. Disc1 is mutated in the 129S6/SvEv strain and modulates working memory in mice. *Proc Natl Acad Sci USA* 103, 3693-3697 (2006).

51 Kvajo, M., McKellar, H., Arguello, P. A., Drew, L. J., Moore, H., MacDermott, A. B., Karayiorgou, M., and Gogos, J. A. A mutation in mouse Disc1 that models a schizophrenia risk allele leads to specific alterations in neuronal architecture and cognition. *Proc Natl Acad Sci USA* 105, 7076-7081 (2008).

52 Li, W., Zhou, Y., Jentsch, J. D., Brown, R. A., Tian, X., Ehninger, D., Hennah, W., Peltonen, L., Lonnqvist, J., Huttunen, M. O., Kaprio, J., Trachtenberg, J. T., Silva, A. J., and Cannon, T. D. Specific developmental disruption of disrupted-in-schizophrenia-1 function results in schizophrenia-related phenotypes in mice. *Proc Natl Acad Sci USA* 104, 18280-18285 (2007).

53 Niwa, M., Kamiya, A., Murai, R., Kubo, K., Gruber, A. J., Tomita, K., Lu, L., Tomisato, S., Jaaro-Peled, H., Seshadri, S., Hiyama, H., Huang, B., Kohda, K., Noda, Y., O'Donnell, P., Nakajima, K., Sawa, A., and Nabeshima, T. Knockdown of DISC1 by in utero gene transfer disturbs postnatal dopaminergic maturation in the frontal cortex and leads to adult behavioral deficits. *Neuron* 65, 480-489 (2010).

54 Pletnikov, M. V., Ayhan, Y., Xu, Y., Nikolskaia, O., Ovanesov, M., Huang, H., Mori, S., Moran, T. H., and Ross, C. A. Enlargement of the lateral ventricles in mutant DISC1 transgenic mice. *Mol Psychiatry* 13, 115 (2008).

55 Shen, S., Lang, B., Nakamoto, C., Zhang, F., Pu, J., Kuan, S. L., Chatzi, C., He, S., Mackie, I., Brandon, N. J., Marquis, K. L., Day, M., Hurko, O., McCaig, C. D., Riedel, G., and St Clair, D. Schizophrenia-related neural and behavioral phenotypes in transgenic mice expressing truncated Disc1. *J Neurosci* 28, 10893-10904 (2008).

56 Ellison-Wright, I., Glahn, D. C., Laird, A. R., Thelen, S. M., and Bullmore, E. The anatomy of first-episode and chronic schizophrenia: an anatomical likelihood estimation meta-analysis. *Am J Psychiatry* 165, 1015-1023 (2008).

57 Olde Loohuis, N. F., Kos, A., Martens, G. J., Van Bokhoven, H., Nadif Kasri, N., and Aschrafi, A. MicroRNA networks direct neuronal development and plasticity. *Cell Mol Life Sci* 69, 89-102 (2012).

58 Kocerha, J., Faghihi, M. A., Lopez-Toledano, M. A., Huang, J., Ramsey, A. J., Caron, M. G., Sales, N., Willoughby, D., Elmen, J., Hansen, H. F., Orum, H., Kauppinen, S., Kenny, P. J., and Wahlestedt, C. MicroRNA-219 modulates NMDA receptor-mediated neurobehavioral dysfunction. *Proc Natl Acad Sci USA* 106, 3507-3512 (2009).

59 Flagstad, P., Mork, A., Glenthoj, B. Y., van Beek, J., Michael-Titus, A. T., and Didriksen, M. Disruption of neurogenesis on gestational day 17 in the rat causes behavioral changes relevant to positive and negative schizophrenia symptoms and alters amphetamine-induced dopamine release in nucleus accumbens. *Neuropsychopharmacology* 29, 2052-2064 (2004).

60 Newton, S. S. and Duman, R. S. Neurogenic actions of atypical antipsychotic drugs and therapeutic implications. *CNS Drugs* 21, 715-725 (2007).

61 Brennand, K., Savas, J. N., Kim, Y., Tran, N., Simone, A., Hashimoto-Torii, K., Beaumont, K. G., Kim, H. J., Topol, A., Ladran, I., Abdelrahim, M., Matikainen-Ankney, B., Chao, S. H., Mrksich, M., Rakic, P., Fang, G., Zhang, B., Yates, J. R., 3rd, and Gage, F. H. Phenotypic differences in hiPSC NPCs derived from patients with schizophrenia. *Mol Psychiatry* 20, 361-368 (2014).

62 Yoon, K. J., Nguyen, H. N., Ursini, G., Zhang, F., Kim, N. S., Wen, Z., Makri, G., Nauen, D., Shin, J. H., Park, Y., Chung, R., Pekle, E., Zhang, C., Towe, M., Hussaini, S. M., Lee, Y., Rujescu, D., St Clair, D., Kleinman, J. E., Hyde, T. M., Krauss, G., Christian, K. M., Rapoport, J. L., Weinberger, D. R., Song, H., and Ming, G. L. Modeling a genetic risk for schizophrenia in iPSCs and mice reveals neural stem cell deficits associated with adherens junctions and polarity. *Cell Stem Cell* 15, 79-91 (2014).

63 Sun, G., Ye, P., Murai, K., Lang, M. F., Li, S., Zhang, H., Li, W., Fu, C., Yin, J., Wang, A., Ma, X., and Shi, Y. miR-137 forms a regulatory loop with nuclear receptor TLX and LSD1 in neural stem cells. *Nat Commun* 2, 529 (2011).

64 Lee, Y., Ahn, C., Han, J., Choi, H., Kim, J., Yim, J., Lee, J., Provost, P., Radmark, O., Kim, S., and Kim, V. N. The nuclear RNase III Drosha initiates microRNA processing. *Nature* 425, 415-419 (2003).

65 Sun, G., Yeh, S. Y., Yuan, C. W., Chiu, M. J., Yung, B. S., and Yen, Y. Molecular Properties, Functional Mechanisms, and Applications of Sliced siRNA. *Mol Ther Nucleic Acids* 4, e221 (2015).

66 Kim, J. Y., Duan, X., Liu, C. Y., Jang, M. H., Guo, J. U., Pow-anpongkul, N., Kang, E., Song, H., and Ming, G. L. DISC1 regulates new neuron development in the adult brain via modulation of AKT-mTOR signaling through KIAA1212. *Neuron* 63, 761-773 (2009).

67 Abmayr, S. M., Yao, T., Parmely, T., and Workman, J. L. Preparation of nuclear and cytoplasmic extracts from mammalian cells. *Curr Protoc Pharmacol* Chapter 12, Unit12 13 (2006).

68 Keene, J. D., Komisarow, J. M., and Friedersdorf, M. B. RIP-Chip: the isolation and identification of mRNAs, microRNAs and protein components of ribonucleoprotein complexes from cell extracts. *Nat Protoc* 1, 302-307 (2006).

I claim:

1. A method of correcting a defective rate of proliferation in a population of neural stem cells (NSCs) comprising:
   contacting the population of NSCs with an effective amount of an miR-219 specific inhibitor, wherein the miR-219 specific inhibitor causes an increase in NSC proliferation rate.

2. The method of claim 1, wherein contact of the population of NSCs with the miR-219 specific inhibitor takes place in vitro or in vivo.

3. The method of claim 2, wherein the population of NSCs is derived from a subject suffering from schizophrenia, bipolar disorder, or depression.

4. The method of claim 1, wherein the miR-219 specific inhibitor is a tough decoy RNA, an RNAi molecule, an aptamer, an miR-219-5p hairpin inhibitor, or TuD-miR-219.

5. The method of claim 1, further comprising contacting the population of NSCs with an effective amount of an agent to increase expression or activity of TX, wherein the agent is a vector expressing a gene encoding TLX.

6. A method of treating a neurodevelopmental disorder in a subject comprising:
   administering a therapeutically effective dose of a pharmaceutical composition to the subject, the pharmaceutical composition comprising an miR-219 specific inhibitor, wherein the miR-219 specific inhibitor maintains normal NSC proliferation in the subject.

7. The method of claim 6, wherein the subject is suffering from schizophrenia, bipolar disorder, or depression.

8. The method of claim 6, wherein the miR-219 specific inhibitor is a tough decoy RNA, an RNAi molecule, an aptamer, an miR-219-5p hairpin inhibitor, or TuD-miR-219.

9. The method of claim 6, wherein the pharmaceutical composition further comprises an agent to increase expression or activity of TLX, wherein the agent is a vector expressing a gene encoding TLX.

10. The method of claim 6, further comprising administering a therapeutically effective dose of a second pharmaceutical composition to the subject, the pharmaceutical composition comprising an agent to increase expression or activity of TLX, wherein the agent is a vector expressing a gene encoding TLX.

11. The method of claim 6, wherein administration of the pharmaceutical composition is an oral, intravenous, intrathecal, or intracranial route of administration.

* * * * *

UNITED STATES PATENT AND TRADEMARK OFFICE
CERTIFICATE OF CORRECTION

PATENT NO. : 11,013,753 B2  
APPLICATION NO. : 16/083849  
DATED : May 25, 2021  
INVENTOR(S) : Yanhong Shi Page 1 of 1

It is certified that error appears in the above-identified patent and that said Letters Patent is hereby corrected as shown below:

In the Specification

Statement of Government Interest section, Column 1, Lines 15-21, please delete:
"This work was supported by Sidell Kagan Foundation and California Institute for Regenerative Medicine TR2-01832 and RB4-06277. Research included work performed in Integrative Genomics and Drug Discovery & Structural Biology Cores supported by the National Cancer Institute of the National Institutes of Health under award number P30CA33572."

And insert:
--This invention was made with government support under P30 CA033572 awarded by the National Institutes of Health. The government has certain rights in the invention.--

Signed and Sealed this  
Twenty-fourth Day of December, 2024

Derrick Brent  
*Acting Director of the United States Patent and Trademark Office*

SEQUENCE LISTING

<160> NUMBER OF SEQ ID NOS: 49

<210> SEQ ID NO 1
<211> LENGTH: 21
<212> TYPE: DNA
<213> ORGANISM: Artificial Sequence
<220> FEATURE:
<223> OTHER INFORMATION: miR-219 antisense northern blot probe

<400> SEQUENCE: 1
agaattgcgt ttggacaatc a                                       21

<210> SEQ ID NO 2
<211> LENGTH: 20
<212> TYPE: DNA
<213> ORGANISM: Artificial Sequence
<220> FEATURE:
<223> OTHER INFORMATION: U6 antisense northern blot probe

<400> SEQUENCE: 2
tatggaacgc ttctcgaatt                                         20

<210> SEQ ID NO 3
<211> LENGTH: 22
<212> TYPE: DNA
<213> ORGANISM: Artificial Sequence
<220> FEATURE:
<223> OTHER INFORMATION: mTLX forward RT-PCR primer

<400> SEQUENCE: 3
gtctttacaa gatcagctga tg                                      22

<210> SEQ ID NO 4
<211> LENGTH: 23
<212> TYPE: DNA
<213> ORGANISM: Artificial Sequence
<220> FEATURE:
<223> OTHER INFORMATION: mTLX reverse RT-PCR primer

<400> SEQUENCE: 4
atgtcactgg atttgtacat atc                                     23

<210> SEQ ID NO 5
<211> LENGTH: 21
<212> TYPE: DNA
<213> ORGANISM: Artificial Sequence
<220> FEATURE:
<223> OTHER INFORMATION: pri-miR-219-1 forward RT-PCR primer

<400> SEQUENCE: 5
tttcccacgc cagacattca c                                       21

<210> SEQ ID NO 6
<211> LENGTH: 21
<212> TYPE: DNA
<213> ORGANISM: Artificial Sequence
<220> FEATURE:
<223> OTHER INFORMATION: pri-miR-219-1 reverse RT-PCR primer

<400> SEQUENCE: 6
gatccccaac ttctctcaag c                                       21

<210> SEQ ID NO 7
<211> LENGTH: 21
<212> TYPE: DNA
<213> ORGANISM: Artificial Sequence

```
<220> FEATURE:
<223> OTHER INFORMATION: pri-miR-219-2 forward RT-PCR primer

<400> SEQUENCE: 7
ttgccgagct tctgcgaggt a                                          21

<210> SEQ ID NO 8
<211> LENGTH: 21
<212> TYPE: DNA
<213> ORGANISM: Artificial Sequence
<220> FEATURE:
<223> OTHER INFORMATION: pri-miR-219-2 reverse RT-PCR primer

<400> SEQUENCE: 8
tgtcccctct ttgcatgcca g                                          21

<210> SEQ ID NO 9
<211> LENGTH: 21
<212> TYPE: DNA
<213> ORGANISM: Artificial Sequence
<220> FEATURE:
<223> OTHER INFORMATION: PDGFRalpha forward RT-PCR primer

<400> SEQUENCE: 9
caaacctgac catgccacca g                                          21

<210> SEQ ID NO 10
<211> LENGTH: 21
<212> TYPE: DNA
<213> ORGANISM: Artificial Sequence
<220> FEATURE:
<223> OTHER INFORMATION: PDGFRalpha reverse RT-PCR primer

<400> SEQUENCE: 10
tctcgatggc actctcttcc g                                          21

<210> SEQ ID NO 11
<211> LENGTH: 21
<212> TYPE: DNA
<213> ORGANISM: Artificial Sequence
<220> FEATURE:
<223> OTHER INFORMATION: RORbeta forward RT-PCR primer

<400> SEQUENCE: 11
tacgtggtgg agttcgccaa g                                          21

<210> SEQ ID NO 12
<211> LENGTH: 21
<212> TYPE: DNA
<213> ORGANISM: Artificial Sequence
<220> FEATURE:
<223> OTHER INFORMATION: RORbeta reverse RT-PCR primer

<400> SEQUENCE: 12
cccatgcaag ttgcagactg c                                          21

<210> SEQ ID NO 13
<211> LENGTH: 23
<212> TYPE: DNA
<213> ORGANISM: Artificial Sequence
<220> FEATURE:
<223> OTHER INFORMATION: LMO3 forward RT-PCR primer

<400> SEQUENCE: 13
gtttggtgta acgggaaact gcg                                        23
```

<210> SEQ ID NO 14
<211> LENGTH: 23
<212> TYPE: DNA
<213> ORGANISM: Artificial Sequence
<220> FEATURE:
<223> OTHER INFORMATION: LMO3 reverse RT-PCR primer

<400> SEQUENCE: 14
tcctcgtagt ctgtctggca aag         23

<210> SEQ ID NO 15
<211> LENGTH: 21
<212> TYPE: DNA
<213> ORGANISM: Artificial Sequence
<220> FEATURE:
<223> OTHER INFORMATION: HMGA2 forward RT-PCR primer

<400> SEQUENCE: 15
acatcagccc agggacaacc t           21

<210> SEQ ID NO 16
<211> LENGTH: 21
<212> TYPE: DNA
<213> ORGANISM: Artificial Sequence
<220> FEATURE:
<223> OTHER INFORMATION: HMGA2 reverse RT-PCR primer

<400> SEQUENCE: 16
caagagtccg cagaggagga t           21

<210> SEQ ID NO 17
<211> LENGTH: 21
<212> TYPE: DNA
<213> ORGANISM: Artificial Sequence
<220> FEATURE:
<223> OTHER INFORMATION: EphrinB2 forward RT-PCR primer

<400> SEQUENCE: 17
ttcagcccta acctctgggg t           21

<210> SEQ ID NO 18
<211> LENGTH: 21
<212> TYPE: DNA
<213> ORGANISM: Artificial Sequence
<220> FEATURE:
<223> OTHER INFORMATION: EphrinB2 reverse RT-PCR primer

<400> SEQUENCE: 18
aacccaggag attgttcccg g           21

<210> SEQ ID NO 19
<211> LENGTH: 20
<212> TYPE: DNA
<213> ORGANISM: Artificial Sequence
<220> FEATURE:
<223> OTHER INFORMATION: mGAPDH forward RT-PCR primer

<400> SEQUENCE: 19
catcaccatc ttccaggagc            20

<210> SEQ ID NO 20
<211> LENGTH: 21
<212> TYPE: DNA
<213> ORGANISM: Artificial Sequence
<220> FEATURE:
<223> OTHER INFORMATION: mGAPDH reverse RT-PCR primer -continued

<400> SEQUENCE: 20
gctgtagccg tattcattgt c                                          21

<210> SEQ ID NO 21
<211> LENGTH: 23
<212> TYPE: DNA
<213> ORGANISM: Artificial Sequence
<220> FEATURE:
<223> OTHER INFORMATION: pri-miR-219-2 forward RT-PCR primer

<400> SEQUENCE: 21
tacgcagctc ccgagatctg gtg                                        23

<210> SEQ ID NO 22
<211> LENGTH: 23
<212> TYPE: DNA
<213> ORGANISM: Artificial Sequence
<220> FEATURE:
<223> OTHER INFORMATION: pri-miR-219-2 reverse RT-PCR primer

<400> SEQUENCE: 22
cagcgtggac ctcgtctctg tag                                        23

<210> SEQ ID NO 23
<211> LENGTH: 24
<212> TYPE: DNA
<213> ORGANISM: Artificial Sequence
<220> FEATURE:
<223> OTHER INFORMATION: pre-miR-219-2 forward RT-PCR primer

<400> SEQUENCE: 23
ctgattgtcc aaacgcaatt cttg                                       24

<210> SEQ ID NO 24
<211> LENGTH: 22
<212> TYPE: DNA
<213> ORGANISM: Artificial Sequence
<220> FEATURE:
<223> OTHER INFORMATION: pre-miR-219-2 reverse RT-PCR primer

<400> SEQUENCE: 24
cagatgtcca gccacaattc tc                                         22

<210> SEQ ID NO 25
<211> LENGTH: 22
<212> TYPE: DNA
<213> ORGANISM: Artificial Sequence
<220> FEATURE:
<223> OTHER INFORMATION: PDGFRalpha forward RT-PCR primer

<400> SEQUENCE: 25
gtggcctgga cgaacagaga ct                                         22

<210> SEQ ID NO 26
<211> LENGTH: 22
<212> TYPE: DNA
<213> ORGANISM: Artificial Sequence
<220> FEATURE:
<223> OTHER INFORMATION: PDGFRalpha reverse RT-PCR primer

<400> SEQUENCE: 26
ggaacctgtc tcgatggcac tc                                         22

<210> SEQ ID NO 27

```
<211> LENGTH: 23
<212> TYPE: DNA
<213> ORGANISM: Artificial Sequence
<220> FEATURE:
<223> OTHER INFORMATION: m TLX forward RT-PCR primer

<400> SEQUENCE: 27
ggttcagaca gctccgatta gac                                             23

<210> SEQ ID NO 28
<211> LENGTH: 23
<212> TYPE: DNA
<213> ORGANISM: Artificial Sequence
<220> FEATURE:
<223> OTHER INFORMATION: m TLX reverse RT-PCR primer

<400> SEQUENCE: 28
tggagagcgg caatggcggc agc                                             23

<210> SEQ ID NO 29
<211> LENGTH: 20
<212> TYPE: DNA
<213> ORGANISM: Artificial Sequence
<220> FEATURE:
<223> OTHER INFORMATION: beta-Actin forward RT-PCR primer

<400> SEQUENCE: 29
ccgagcgtgg ctacagcttc                                                 20

<210> SEQ ID NO 30
<211> LENGTH: 20
<212> TYPE: DNA
<213> ORGANISM: Artificial Sequence
<220> FEATURE:
<223> OTHER INFORMATION: beta-Actin reverse RT-PCR primer

<400> SEQUENCE: 30
acctggccgt caggcagctc                                                 20

<210> SEQ ID NO 31
<211> LENGTH: 20
<212> TYPE: DNA
<213> ORGANISM: Artificial Sequence
<220> FEATURE:
<223> OTHER INFORMATION: hTLX forward RT-PCR primer

<400> SEQUENCE: 31
ctaagagtgt gccagccttc                                                 20

<210> SEQ ID NO 32
<211> LENGTH: 21
<212> TYPE: DNA
<213> ORGANISM: Artificial Sequence
<220> FEATURE:
<223> OTHER INFORMATION: hTLX reverse RT-PCR primer

<400> SEQUENCE: 32
tgttagcatc aaccggaatg g                                               21

<210> SEQ ID NO 33
<211> LENGTH: 19
<212> TYPE: DNA
<213> ORGANISM: Artificial Sequence
<220> FEATURE:
<223> OTHER INFORMATION: hGAPDH forward RT-PCR primer

<400> SEQUENCE: 33
```

```
cctgttcgac agtcagccg                                                 19

<210> SEQ ID NO 34
<211> LENGTH: 19
<212> TYPE: DNA
<213> ORGANISM: Artificial Sequence
<220> FEATURE:
<223> OTHER INFORMATION: hGAPDH reverse RT-PCR primer

<400> SEQUENCE: 34
cgaccaaatc cgttgactc                                                 19

<210> SEQ ID NO 35
<211> LENGTH: 99
<212> TYPE: DNA
<213> ORGANISM: Artificial Sequence
<220> FEATURE:
<223> OTHER INFORMATION: TuD-miR-219

<400> SEQUENCE: 35
gacggcgcta ggatcatcaa cctcgagcgc tagcaagtat tctggtcaca gaatacaacg    60
tcgaccacta gtcaagatga tcctagcgcc gtctttttt                           99

<210> SEQ ID NO 36
<211> LENGTH: 1158
<212> TYPE: DNA
<213> ORGANISM: Homo sapiens

<400> SEQUENCE: 36
atgagcaagc cagccggatc aacaagccgc attttagata tccctgcaa agtgtgtggc     60 gaccgcagct cggggaagca ctacggggtc tacgcctgcg acggctgctc aggtttttc    120 aaacggagca tccgaaggaa taggacctat gtctgcaaat ctggaaacca gggaggctgt   180
ccggtggaca agacgcacag aaaccagtgc agggcgtgtc ggctgaagaa gtgtttggaa   240
gtcaacatga caaagacgc cgtgcagcac gagcgggggc ctcggacgtc caccatccgc    300
aagcaagtgg ccctctactt ccgtggacac aaggaggaga acgggccgc cgcgcacttt    360 ccctcggcgg cgctccctgc gccggccttc ttcaccgcgg tcacgcagct ggagccgcac   420
ggcctggagc tggccgcggt gtccaccact ccagagcggc agaccctcgt gagcctggct   480
cagcccacgc ccaagtaccc ccatgaagtg aatgggaccc caatgtatct ctatgaagtg   540
gccacggagt cggtgtgtga atcagctgcc agacttctct tcatgagcat caagtgggct   600
aagagtgtgc cagccttctc cacgctgtct ttgcaagacc agctgatgct tttggaagat   660
gcttggagag aactgtttgt tctaggaata gcacaatggg ccattccggt tgatgctaac   720
actctactgg ctgtatctgg catgaacggt gacaacacag attcccagaa gctgaacaag   780
atcatatctg aaatacaggc tttacaagag gtggtggctc gatttagaca actccggtta   840
gatgctactg aatttgcctg tctaaaatgc atcgtcactt tcaaagccgt tcctacacat   900
agtggttctg aactgagaag tttccggaat gctgccgcca ttgcagccct tcaagatgag   960
gctcagctaa cgctcaacag ctacatccat accagatatc ccactcaacc ctgtcgcttt  1020
ggaaaactcc tgttgctttt gccagcttta cgttctatta gccatcaac tatagaagaa  1080 gtgttttca aaaaaaccat cggcaatgtg ccaattacaa gactgctttc agatatgtac   1140
aaatccagtg atatctaa                                                1158

<210> SEQ ID NO 37
```

<211> LENGTH: 385
<212> TYPE: PRT
<213> ORGANISM: Homo sapiens

<400> SEQUENCE: 37

```
Met Ser Lys Pro Ala Gly Ser Thr Ser Arg Ile Leu Asp Ile Pro Cys
1               5                   10                  15

Lys Val Cys Gly Asp Arg Ser Ser Gly Lys His Tyr Gly Val Tyr Ala
            20                  25                  30

Cys Asp Gly Cys Ser Gly Phe Phe Lys Arg Ser Ile Arg Arg Asn Arg
        35                  40                  45

Thr Tyr Val Cys Lys Ser Gly Asn Gln Gly Gly Cys Pro Val Asp Lys
    50                  55                  60

Thr His Arg Asn Gln Cys Arg Ala Cys Arg Leu Lys Lys Cys Leu Glu
65                  70                  75                  80

Val Asn Met Asn Lys Asp Ala Val Gln His Glu Arg Gly Pro Arg Thr
                85                  90                  95

Ser Thr Ile Arg Lys Gln Val Ala Leu Tyr Phe Arg Gly His Lys Glu
            100                 105                 110

Glu Asn Gly Ala Ala Ala His Phe Pro Ser Ala Ala Leu Pro Ala Pro
        115                 120                 125

Ala Phe Phe Thr Ala Val Thr Gln Leu Glu Pro His Gly Leu Glu Leu
    130                 135                 140

Ala Ala Val Ser Thr Thr Pro Glu Arg Gln Thr Leu Val Ser Leu Ala
145                 150                 155                 160

Gln Pro Thr Pro Lys Tyr Pro His Glu Val Asn Gly Thr Pro Met Tyr
                165                 170                 175

Leu Tyr Glu Val Ala Thr Glu Ser Val Cys Glu Ser Ala Ala Arg Leu
            180                 185                 190

Leu Phe Met Ser Ile Lys Trp Ala Lys Ser Val Pro Ala Phe Ser Thr
        195                 200                 205

Leu Ser Leu Gln Asp Gln Leu Met Leu Leu Glu Asp Ala Trp Arg Glu
    210                 215                 220

Leu Phe Val Leu Gly Ile Ala Gln Trp Ala Ile Pro Val Asp Ala Asn
225                 230                 235                 240

Thr Leu Leu Ala Val Ser Gly Met Asn Gly Asp Asn Thr Asp Ser Gln
                245                 250                 255

Lys Leu Asn Lys Ile Ile Ser Glu Ile Gln Ala Leu Gln Glu Val Val
            260                 265                 270

Ala Arg Phe Arg Gln Leu Arg Leu Asp Ala Thr Glu Phe Ala Cys Leu
        275                 280                 285

Lys Cys Ile Val Thr Phe Lys Ala Val Pro Thr His Ser Gly Ser Glu
    290                 295                 300

Leu Arg Ser Phe Arg Asn Ala Ala Ile Ala Ala Leu Gln Asp Glu
305                 310                 315                 320

Ala Gln Leu Thr Leu Asn Ser Tyr Ile His Thr Arg Tyr Pro Thr Gln
                325                 330                 335

Pro Cys Arg Phe Gly Lys Leu Leu Leu Leu Pro Ala Leu Arg Ser
            340                 345                 350

Ile Ser Pro Ser Thr Ile Glu Glu Val Phe Phe Lys Lys Thr Ile Gly
        355                 360                 365

Asn Val Pro Ile Thr Arg Leu Leu Ser Asp Met Tyr Lys Ser Ser Asp
    370                 375                 380

Ile
```

<210> SEQ ID NO 38
<211> LENGTH: 57
<212> TYPE: DNA
<213> ORGANISM: Homo sapiens

<400> SEQUENCE: 38
ggaaaactcc tgttgctttt gccagcttta cgttctatta gcccatcaac tatagaa    57

<210> SEQ ID NO 39
<211> LENGTH: 19
<212> TYPE: PRT
<213> ORGANISM: Homo sapiens

<400> SEQUENCE: 39

Gly Lys Leu Leu Leu Leu Leu Pro Ala Leu Arg Ser Ile Ser Pro Ser
1               5                   10                  15

Thr Ile Glu

<210> SEQ ID NO 40
<211> LENGTH: 8
<212> TYPE: DNA
<213> ORGANISM: Artificial Sequence
<220> FEATURE:
<223> OTHER INFORMATION: miR-219-5P target site

<400> SEQUENCE: 40 gacaatca                                                          8

<210> SEQ ID NO 41
<211> LENGTH: 8
<212> TYPE: DNA
<213> ORGANISM: Artificial Sequence
<220> FEATURE:
<223> OTHER INFORMATION: mutated miR-219-5P target site

<400> SEQUENCE: 41 gatcgtca                                                          8

<210> SEQ ID NO 42
<211> LENGTH: 19
<212> TYPE: PRT
<213> ORGANISM: Artificial Sequence
<220> FEATURE:
<223> OTHER INFORMATION: TLX Dpi peptide

<400> SEQUENCE: 42

Gly Lys Leu Leu Leu Leu Leu Pro Ala Leu Arg Ser Ile Ser Pro Ser
1               5                   10                  15

Thr Ile Glu

<210> SEQ ID NO 43
<211> LENGTH: 23
<212> TYPE: PRT
<213> ORGANISM: Artificial Sequence
<220> FEATURE:
<223> OTHER INFORMATION: TLX control peptide

<400> SEQUENCE: 43

Lys Ser Val Pro Ala Phe Ser Thr Leu Ser Leu Gln Asp Gln Leu Met
1               5                   10                  15

Leu Leu Glu Asp Ala Trp Arg
            20

<210> SEQ ID NO 44
<211> LENGTH: 29
<212> TYPE: DNA
<213> ORGANISM: Artificial Sequence
<220> FEATURE:
<223> OTHER INFORMATION: oligo of TuD-miR-219

<400> SEQUENCE: 44
tcgaagaatt gcgttctgat ggacaatca                              29

<210> SEQ ID NO 45
<211> LENGTH: 29
<212> TYPE: DNA
<213> ORGANISM: Artificial Sequence
<220> FEATURE:
<223> OTHER INFORMATION: oligo of TuD-miR-219

<400> SEQUENCE: 45
ctagtgattg tccatcagaa cgcaattct                              29

<210> SEQ ID NO 46
<211> LENGTH: 33
<212> TYPE: DNA
<213> ORGANISM: Artificial Sequence
<220> FEATURE:
<223> OTHER INFORMATION: primer

<400> SEQUENCE: 46
ttcatagagc tcacaccggc ttgtccacct tac                         33

<210> SEQ ID NO 47
<211> LENGTH: 33
<212> TYPE: DNA
<213> ORGANISM: Artificial Sequence
<220> FEATURE:
<223> OTHER INFORMATION: primer

<400> SEQUENCE: 47
ttcatactcg aggaggatac ggaaagaggc gag                         33

<210> SEQ ID NO 48
<211> LENGTH: 31
<212> TYPE: DNA
<213> ORGANISM: Artificial Sequence
<220> FEATURE:
<223> OTHER INFORMATION: primer

<400> SEQUENCE: 48
gatagctagc aatggcaact ccaagcgtgc t                           31

<210> SEQ ID NO 49
<211> LENGTH: 32
<212> TYPE: DNA
<213> ORGANISM: Artificial Sequence
<220> FEATURE:
<223> OTHER INFORMATION: primer

<400> SEQUENCE: 49
atgaggccga ggtggggctg agtctagaga tc                          32